(12) United States Patent
Jenkins

(10) Patent No.: US 10,203,284 B2
(45) Date of Patent: Feb. 12, 2019

(54) HARDWARE AND MOBILE SOFTWARE FOR OPERATION OF PORTABLE INSTRUMENTS FOR NUCLEIC ACID AMPLIFICATION

(71) Applicant: Diagenetix, Inc., Honolulu, HI (US)

(72) Inventor: Daniel M. Jenkins, Honolulu, HI (US)

(73) Assignee: DIAGENETIX, INC., Honolulu, HI (US)

( * ) Notice: Subject to any disclaimer, the term of this patent is extended or adjusted under 35 U.S.C. 154(b) by 263 days.

(21) Appl. No.: 14/914,571

(22) PCT Filed: Aug. 26, 2014

(86) PCT No.: PCT/US2014/052690
§ 371 (c)(1),
(2) Date: Feb. 25, 2016

(87) PCT Pub. No.: WO2015/031351
PCT Pub. Date: Mar. 5, 2015

(65) Prior Publication Data
US 2016/0216210 A1    Jul. 28, 2016

Related U.S. Application Data

(60) Provisional application No. 61/870,208, filed on Aug. 26, 2013.

(51) Int. Cl.
*G01N 21/64* (2006.01)
*B01L 7/00* (2006.01)
(Continued)

(52) U.S. Cl.
CPC ............ *G01N 21/6486* (2013.01); *B01L 7/52* (2013.01); *C12Q 1/686* (2013.01); *B01L 9/06* (2013.01); *B01L 2200/18* (2013.01); *B01L 2300/023* (2013.01); *B01L 2300/0654* (2013.01); *B01L 2300/1822* (2013.01); *B01L 2300/1827* (2013.01)

(58) Field of Classification Search
CPC ........... B01L 2200/18; B01L 2300/023; B01L 2300/0654; B01L 2300/1822; B01L 2300/1827; B01L 7/52; B01L 9/06; C12Q 1/686; G01N 21/6486
See application file for complete search history.

(56) References Cited

U.S. PATENT DOCUMENTS

2002/0034746 A1\* 3/2002 McMillan ............ C12Q 1/6851
435/6.12
2010/0056383 A1   3/2010 Ririe et al.
(Continued)

FOREIGN PATENT DOCUMENTS

WO         2008060604 A2    5/2008

OTHER PUBLICATIONS

Hoffmann, Global Enclosure Standards Within the Electrical Industry, 2009.
(Continued)

*Primary Examiner* — Gautam Prakash
*Assistant Examiner* — Lydia Edwards
(74) *Attorney, Agent, or Firm* — Pepper Hamilton LLP

(57) ABSTRACT

The present disclosure provides methods and hardware for real-time amplification and detection of nucleic acid molecules.

18 Claims, 23 Drawing Sheets

(51) Int. Cl.
*C12Q 1/686* (2018.01)
*B01L 9/06* (2006.01)
*B01L 99/00* (2010.01)

(56) References Cited

U.S. PATENT DOCUMENTS

2010/0240044 A1    9/2010  Kumar et al.
2011/0005932 A1*   1/2011  Jovanovich ...... G01N 35/00029
                                                        204/453
2011/0312684 A1   12/2011  Moini et al.

OTHER PUBLICATIONS

Idaho Technologies Inc.: Razoe EX Basic Training Workbook, 2011 pp. 1-92.
National Electrical Manufacturers Association: NEMA Standards Publication 250-2003 Enclosures for Electrical Equipment (1000 Volts Maximum), 2003.

* cited by examiner

FIG. 9-Continued
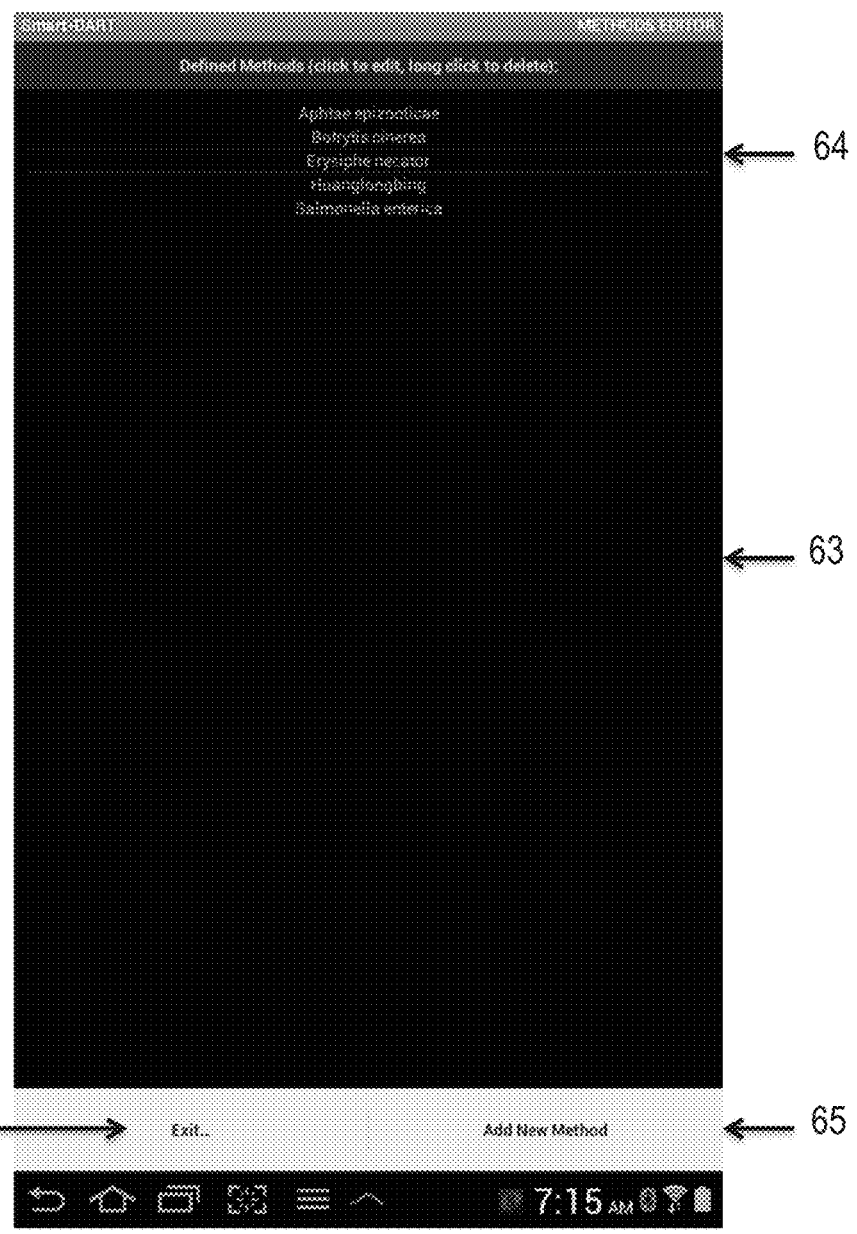

FIG. 9 - Continued

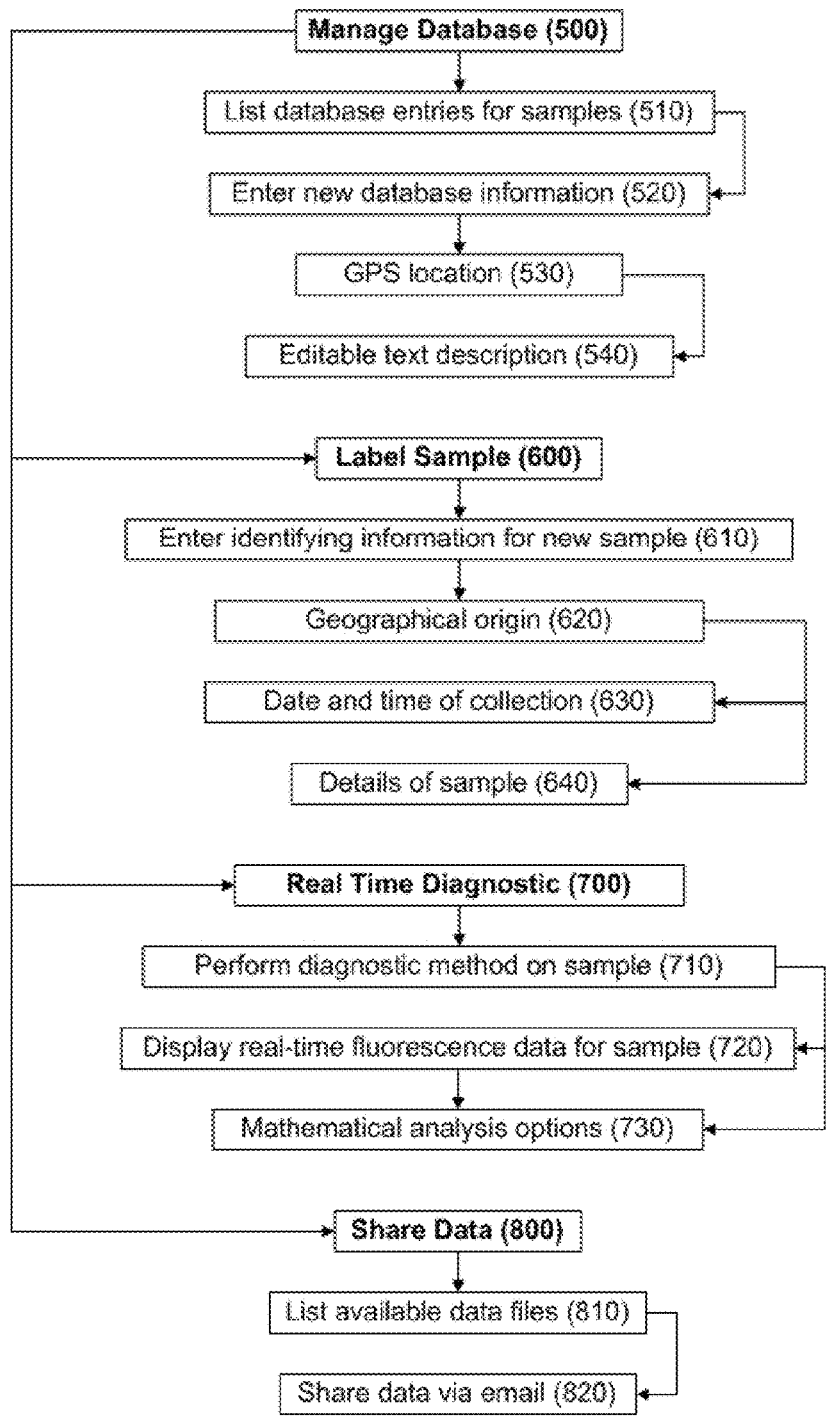
FIG. 17 - Continued

HARDWARE AND MOBILE SOFTWARE FOR OPERATION OF PORTABLE INSTRUMENTS FOR NUCLEIC ACID AMPLIFICATION

FIELD

The present disclosure is directed to methods and hardware for real-time amplification and detection of nucleic acid molecules.

BACKGROUND

Real-time fluorescence based monitoring of nucleic acid amplification is the current state of the art for detecting genes of interest in a sample, for example, to identify presence of a pathogenic organism or a gene linked to certain disease states. Numerous molecular amplification technologies have been coupled to unique fluorescent probe designs which result in increased fluorescence emission as the amplification reaction(s) proceed. Traditionally, diagnostic instruments using these principles used PCR and required rapid thermal cycling, necessitating bulky desktop instruments drawing significant quantities of electrical power from the grid, which were generally confined to the laboratory setting and interfaced to desktop or laptop computers. Improvements in process technology, such as use of isothermal amplification approaches, have enabled the development of simple, low-power, handheld instruments suited for application in remote settings outside of the traditional lab.

There is, however, still a need for improved software and hardware for real time detection of nucleic acid molecules. The present disclosure fulfills these needs and others.

SUMMARY

The present disclosure provides devices configured for detection of amplified nucleic acid molecules comprising: a first housing unit and a second housing unit, wherein the first and second housing units are connectable to each other by a fastener, wherein the interface between the first and second housing units comprises a gasket; wherein the connected first and second housing units enclose the following: a) a reaction block; b) a circuit board electronically connected to the reaction block; and c) a battery electronically connected to the circuit board; wherein the first housing unit comprises an access area for communication with the reaction block; wherein the first housing unit comprises a reaction lid closing off the access with the reaction block; wherein one of the first and second housing units comprises an on/off switch; and wherein one of the first and second housing units comprises a power plug.

In some embodiments, the first or second housing unit further comprises an indicator light. In some embodiments, the indicator light is an LED indicator light connected to the first housing unit, wherein a gasket is between the housing unit and the LED indicator light. In some embodiments, the reaction block further comprises reaction tubes. In some embodiments, the power plug and on/off switch are each connected to the second housing unit, each having a gasket at their interface with the housing unit.

In some embodiments, the reaction block comprises: a first excitation LED panel affixed to a first optic housing unit; a second excitation LED panel affixed to a second optic housing unit; an upper cover comprising one or more gaskets, wherein the upper cover connects the top portions of both the first and second optic housing units; a heating block with one or more reaction tube wells; and a filter holder comprising one or more emission filters, wherein the filter holder connects the bottom portions of the first and second housing units. In some embodiments, the reaction block comprises optional slots for one or more excitation filters.

In some embodiments, the heating block comprises an embedded temperature sensor and an actuator to regulate temperature. In some embodiments, the temperature sensor is a thermocouple, and the actuator is a polyimide film heater. In some embodiments, each of the first and second excitation LED panels are affixed to the first and second optic housing unit, respectively, with a fastener. In some embodiments, the first and second optic housing units comprise a plurality of light pathways configured to transmit light from the first and second LED excitation panels.

In some embodiments, the reaction block comprises: a first bank of light source and a second bank of light source on opposite sides of a heated receptacle, wherein the heated receptacle comprises a plurality of transverse orifices, and wherein the heated receptacle comprises a plurality of bottom portals; a first and second excitation filter in light communication between the first bank of light source and the plurality of transverse orifices of the heated receptacle and second bank of light source and the plurality of transverse orifices of the heated receptacle, respectively; a first detector bank and a second detector bank in light communication with the plurality of bottom portals of the heated receptacle; and a first emission filter and a second emission filter in light communication between the plurality of bottom portals of the heated receptacle and the first detector bank and a second detector bank, respectively.

DETAILED DESCRIPTION

The embodiments disclosed herein leverage the functionality of mobile computing platforms (i.e., smart-phones, tablets, external handheld computer, and the like) for operating and managing data obtained from a simple, handheld diagnostic device running isothermal nucleic acid amplification reactions. Exporting these functions to such a mobile computing platform can enable high performance on an intuitive user interface, while dramatically reducing the size, complexity, and cost of the application specific instrument. These advantages, as well as others that are apparent from the description contained here, were not able to be taken advantage prior to the present disclosure.

Figure 1:
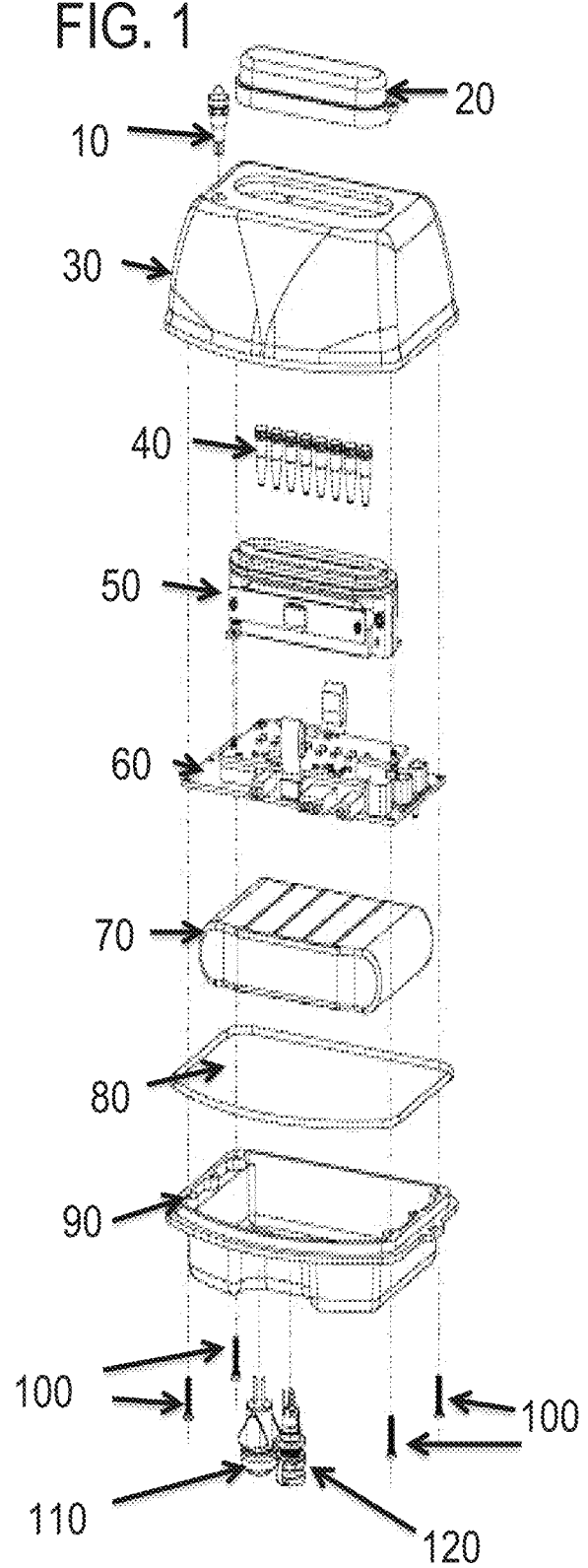
FIG. 1 illustrates a non-limiting implementation of a representative embodiment of a device in three dimensional configuration in an exploded view.

The present disclosure provides devices which are configured for detection of amplified nucleic acid molecules. A representative device is shown in FIG. 1, which illustrates an exploded view of device that can be used to detect multiple amplified nucleic acid molecules in a plurality of samples. In some embodiments, a representative device comprises a first housing unit (30) and a second housing unit (90). In some embodiments, the first and second housing units are connected to each other by one or more fastener(s) (100). Any type of fastener, such as a screw, can be used. In some embodiments, the interface between the first and second housing units comprises a gasket (80).

In some embodiments, one of the first and second housing units comprises a power on/off switch (110), and one of the first and second housing units comprises a power plug (120). In some embodiments, the power plug and power on/off switch are each connected to the second housing unit. In some embodiments, a gasket is placed between the power plug and the housing unit. In some embodiments, a gasket is placed between the on/off switch and the housing unit. In some embodiments, the power on/off switch may be a toggle switch to directly modulate power to the device, or it may be a momentary contact switch implemented as a "soft" switch. In this latter implementation, for example, the contact can modulate the signal to a high side transistor switch powering the circuit, with the device controller latching the signal "on" through a separate path during startup. The signal from the contact switch can then be monitored for activity to unlatch the controller signal to turn itself off if certain conditions are met (e.g., after release if the contact switch is held down for a certain period of time and a reaction is not ongoing). In addition, the "soft" switch configuration can be used to enable the device to shut itself down automatically to conserve a battery, for example in cases when the device is on but idle for an extended period of time. The power plug can be used to connect the device to a power unit or electrical outlet. In some embodiments, the power plug can be used to supply power to operate the device. In some embodiments, the power plug can also be used to recharge a battery.

In some embodiments, the first or second housing unit further comprises an indicator light (10). In some embodiments, the indicator light is an LED indicator light connected to the first housing unit. In some embodiments, a gasket is present between the housing unit and the LED indicator light. The indicator light can be in communication with the circuit board to easily and visibly communicate to a user of the device the status of the reaction and/or detection. For example, in some embodiments, a multicolor LED is used to display a color coded power and connection status. In this implementation, a first color, such as green, may indicate that the device is on and in idle or standby mode; a second color, such as blue, may indicate that the device has an active wireless connection to an external mobile device; and a third color, such as red, may indicate that a reaction is on-going within the device. In some embodiments, the status LED is pulsed with a duty cycle proportional to the remaining battery charge so that the user can rapidly estimate the charge state. The indicator light can be mounted in the first housing unit or anywhere else on the surface of the device, using of a gasket to exclude ingress of dust, light, moisture, or other contaminants.

In some embodiments, when connected by the fastener(s), the first and second housing units enclose a reaction block (50), a circuit board (60), and a battery (70). In some embodiments, the circuit board is electronically connected to the reaction block and the battery. In some embodiments, the circuit board can be configured to operate the device and to communicate with an external or internal user interface. Any battery can be used as long as it has sufficient energy and current rating to power the device. The battery can be permanent (i.e., not able to be replaced) or replaceable. In some embodiments, the battery is rechargeable. In some embodiments, the battery is not rechargeable. In some embodiments, the second housing unit comprises elevated ridges which allow the battery to sit therein raised above the lower most portion of the second housing unit. In some embodiments, the first housing unit comprises an access area for communication with the reaction block. In some embodiments, the first housing unit comprises a reaction lid (20) that closes off the access to the reaction block. The reaction lid can be removable such that a user can insert one or more reaction tubes into the device. In some embodiments, the reaction block contains one or more reaction tubes (40).

Figure 2:
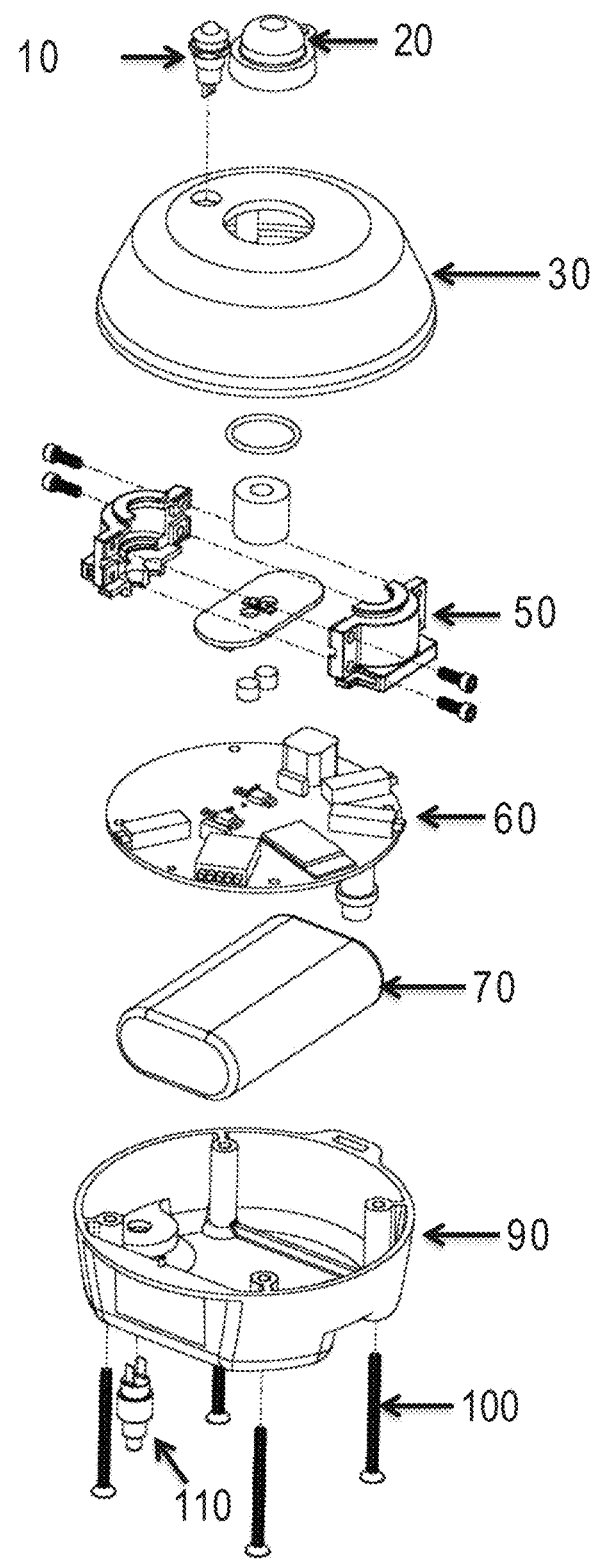
FIG. 2 illustrates another non-limiting implementation of a representative embodiment of a device in three dimensional configuration in an exploded view.

Another representative device is shown in FIG. 2, which contains a single well in the reaction block.

Figure 3:
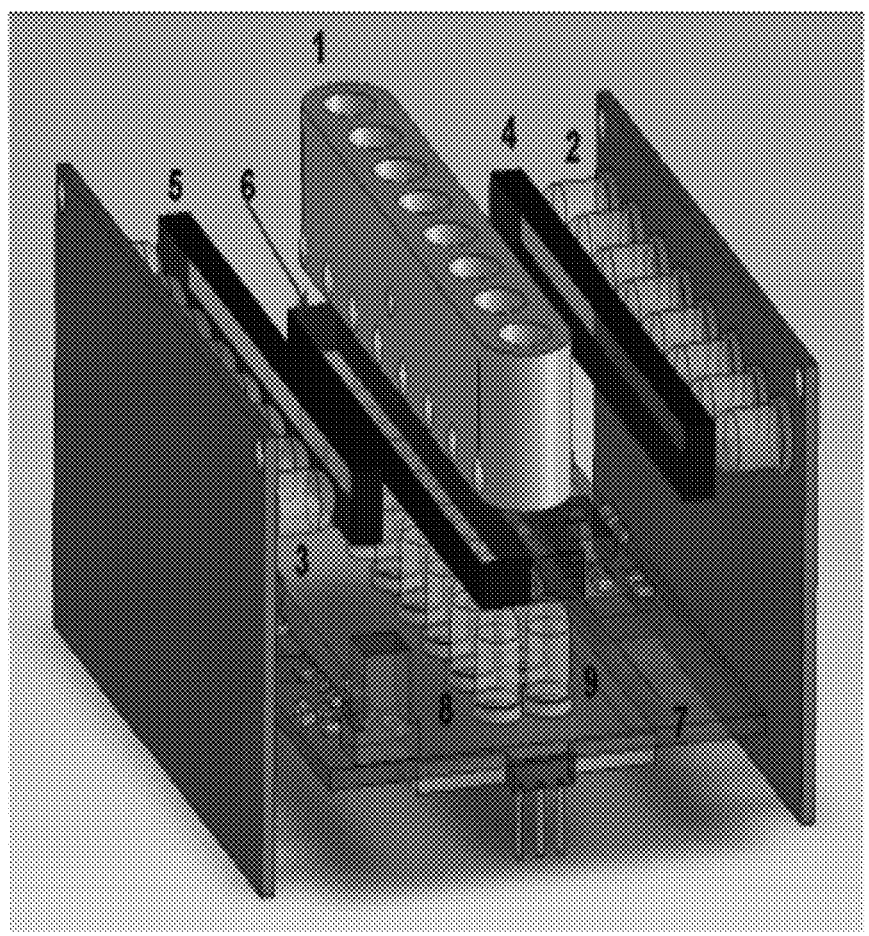
FIG. 3 displays a non-limiting implementation of a representative embodiment of a reaction block in a three dimensional configuration to illustrate relative orientations.

In some embodiments, the reaction block contains components for carrying out nucleic acid amplification reactions. A representative reaction block is shown in FIG. 3. In some embodiments, the reaction block comprises a first bank of light source (2) and a second bank of light source (3) on opposite sides of a heated receptacle (1). In some embodiments, the heated receptacle comprises a plurality of transverse orifices. In some embodiments, the heated receptacle comprises a plurality of bottom portals. In some embodiments, the reaction block further comprises a first excitation filter (4) and a second excitation filter (5) in light communication between the first bank of light source and the plurality of transverse orifices of the heated receptacle and second bank of light source and the plurality of transverse orifices of the heated receptacle, respectively. In some embodiments, the reaction block further comprises a first detector bank (9) and a second detector bank (8) in light communication with the plurality of bottom portals of the heated receptacle. In some embodiments, the reaction block further comprises a first emission filter (7) and a second emission filter (6) in light communication between the plurality of bottom portals of the heated receptacle and the first detector bank and a second detector bank, respectively.

Figure 4:
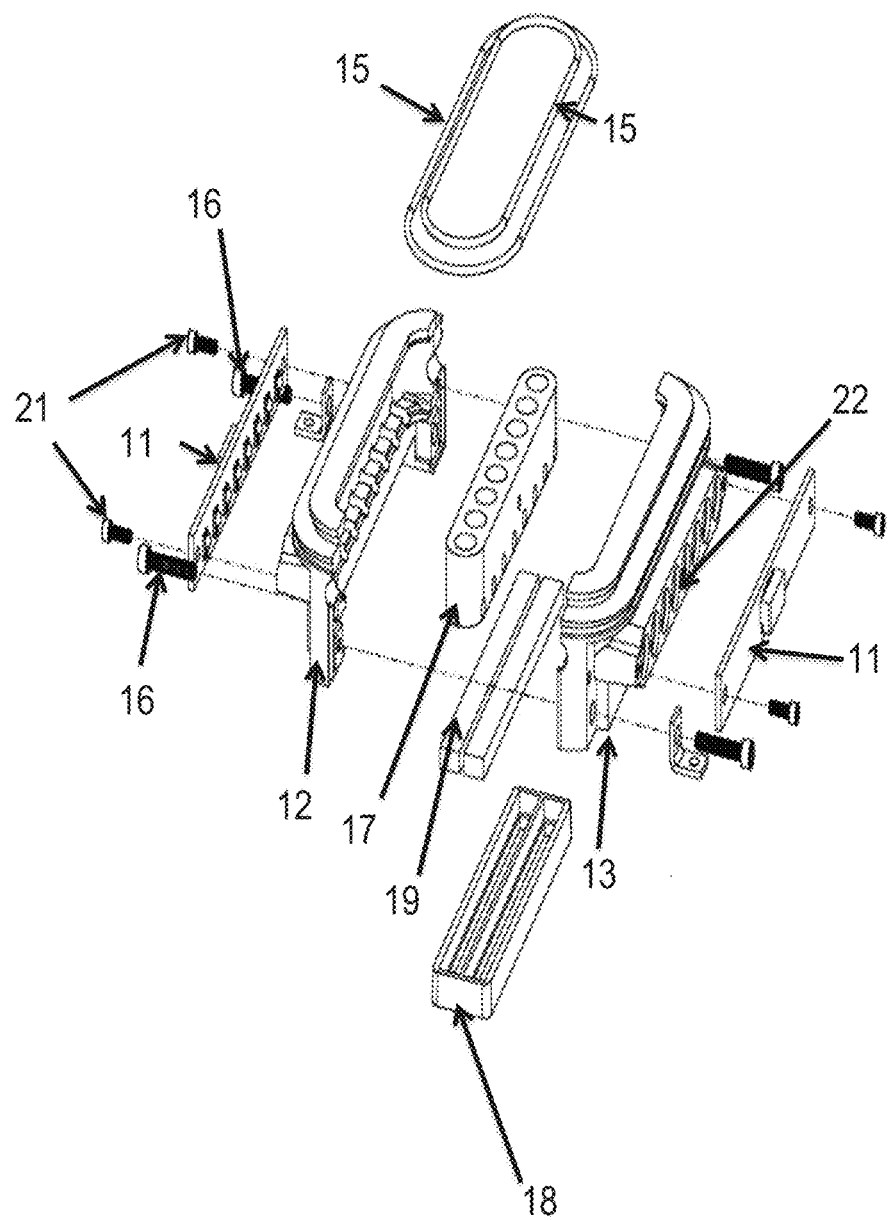
FIG. 4 illustrates a non-limiting implementation of a representative embodiment of a reaction block in a three dimensional configuration for the devices described herein in an exploded view.

Another representative reaction block is shown in FIG. 4. In some embodiments, the reaction block comprises a first excitation LED panel (11) affixed to a first optic housing unit (12) and a second excitation LED panel (11) affixed to a second optic housing unit (13). In some embodiments, the reaction block further comprises an upper cover (14) comprising one or more gaskets (15) that connects the top portions of both the first and second optic housing units. In some embodiments, the first and second housing units are affixed to each other with one or more fastener(s) (16). In some embodiments, the reaction block further comprises a heating block (17) with one or more reaction tube wells to accommodate reaction tubes. The reaction tubes can be any tubes suitable for the reaction or detecting of the amplified nucleic acid molecules. In some embodiments, samples are contained in standard 0.2 ml PCR tubes placed in the heating block. In some embodiments, the reaction block further comprises a filter holder (18) comprising one or more emission filters (19). In some embodiments, the filter holder connects the bottom portions of the first and second housing units. In some embodiments, the optics housing units are accessible through a gasketed opening in the top housing of the device, and the filter holder is inserted into a slot in the bottom of the optics housing above the photodetection circuitry. In some embodiments, each of the first and second excitation LED panels are affixed to the first and second optic housing units, respectively, with one or more fastener(s) (21). In some embodiments, the first and second optic housing units comprise a plurality of light pathways (22) configured to transmit light from the first and second LED excitation panels. The light pathways are essentially voids in the housings that allow the light to be transmitted onto the samples in the reaction tubes facilitating the detection and analysis of the amplification products.

In some embodiments, the heating block further comprises an embedded temperature sensor (not shown) and an actuator (not shown) to regulate temperature. The temperature sensor may be any technology used for measuring temperature including, but not limited to, any thermocouple, thermistor, solid state sensor, infrared thermometer/pyrometer, or resistive temperature device. The temperature actuator may be based on any technology for generating or transporting heat including, but not limited to, resistive heaters, thermoelectric devices, or evaporators or condensors of a refrigerator unit. In some embodiments, temperature measured on an integral Type K thermocouple is compared to a desired temperature, and the difference is used to control the current through a (resistive) polyimide film heater to achieve the desired temperature. In some embodiments, the temperature sensor is a thermocouple, and the actuator is a polyimide film heater.

In some embodiments, multiple emission filters are used to measure different fluorescence spectra, for example, from different fluorescent dyes used in multiplexed amplification reactions. In some embodiments these filters are dichroic or interference filters.

In some embodiments, the first excitation LED panel is affixed to one mount on the first optics housing with a fastener or set of fasteners. In some embodiments, the second excitation LED panel is affixed to a separate mount on the second optics housing with its own fastener or set of fasteners. The excitation LED panel can be configured in any manner such that the light being emitted from the LED panel is directed onto the samples within the reaction tubes such that the reactions can be analyzed and detected. In some embodiments, they are fastened with screws, although the specific type of fastener is not critical and any type of fastener or locking mechanism can be used.

To measure fluorescence in the reaction block, samples in the reaction tubes are illuminated by spectrally limited light sources, and the resulting fluorescence emission is detected by corresponding photodetectors. The light sources for sample illumination may include any technology to generate light in the visible, UV, or IR spectrum, including LEDs, lasers, incandescent, or other lamp technologies, with or without the use of excitation filters to limit the excitation spectra. Photodetectors may include any type of photodiode, photoemissive sensor, photomultiplier tube, photoconductive cell, or other light sensitive element.

For sensitive yet inexpensive detection, individual photosensors may be low dark current lensed photodiodes with each interfaced to an electrometer grade operational amplifier in a transimpedance configuration using conductive guards surrounding the photodetector and amplifier input pins. This is can be used to prevent leakage of signals from one detector through the forward conduction path of other detectors. Voltages from each photoamplifier are then summed into a common junction using a standard voltage summing amplifier, and subsequent hardware filter and amplification stages to enable programmable gain using the full resolution of the analog to digital conversion on the microcontroller. Alternately, individual photodetectors can be multiplexed to the amplifier and readout circuitry using the same addressing signals used for LED illumination, improving signal to noise ratio by not superimposing noise from non-specific detectors.

The present disclosure also provides embodiments of circuitry that can be used to detect nucleic acid molecules. In some embodiments, the complexity of multiplexing the fluorescence detection from an array of samples or optical channels is reduced by summing all detector signals into a single signal processing path, and implementing the multiplexing in the time domain by sequentially illuminating each sample or optical channel with discrete, addressable light sources. As the signal processing is the most hardware intensive aspect of the luminescence detection, integrating all channels onto a single processing path significantly simplifies the hardware and space requirements for the design using a rugged array of rigidly mounted components. Accordingly, in some embodiments, the detector signals are analyzed from a single processing path. Alternatively, individual detectors corresponding to the illuminating light sources can be multiplexed to the readout circuitry using the same addressing signals used for sample illumination, which can result in improved signal to noise ratio with a very small incremental cost/complexity.

Figure 5:
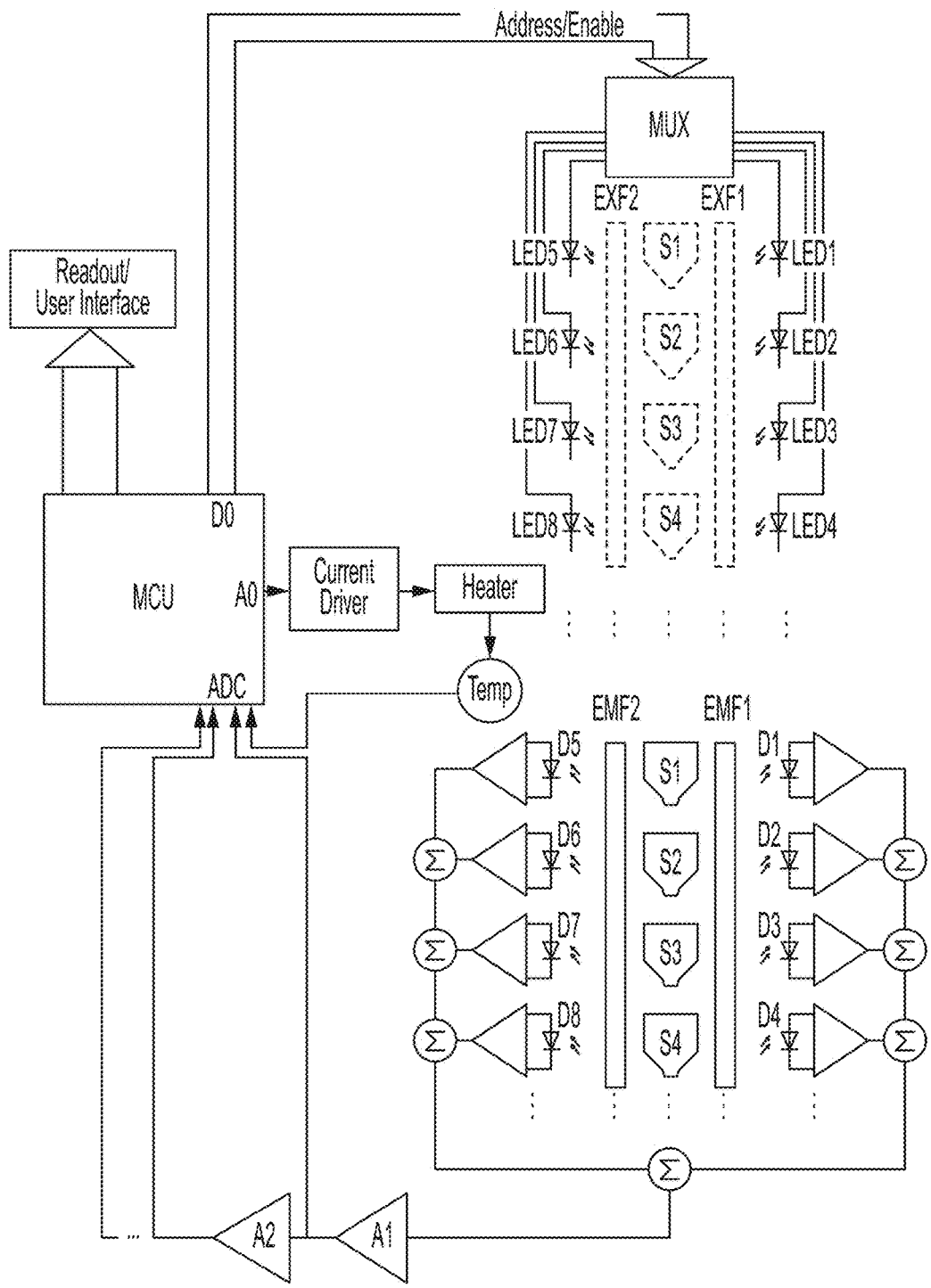
FIG. 5 illustrates a representative example of general circuit implementation for the time domain multiplexing, in which multiple samples and/or optical channels are illuminated sequentially in time from banks of light sources (LED1-LED8 . . . ), with all of emitted radiation monitored by a single bank of detectors (D1-D8) interfaced through a common summing junction to a single signal processing path.
Figure 6:
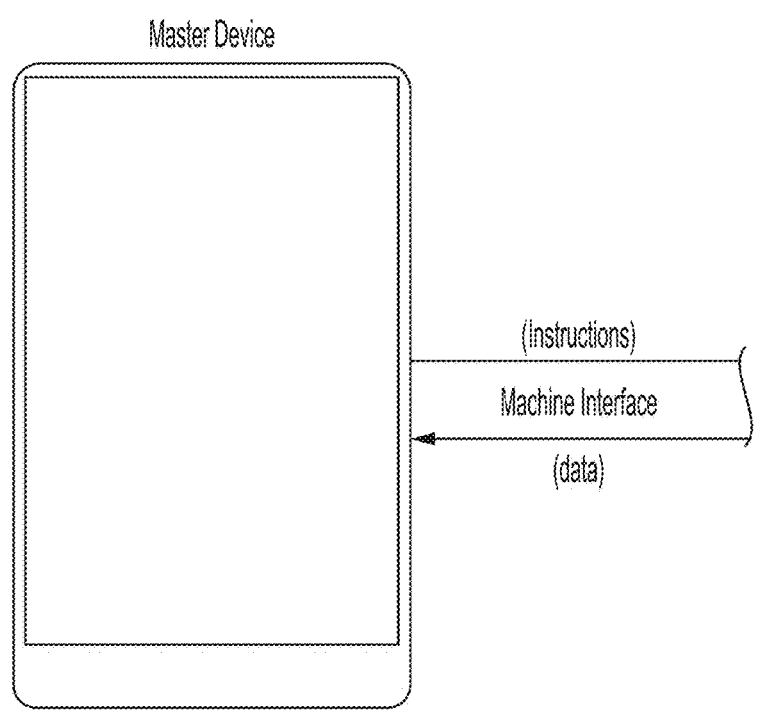
FIG. 6 illustrates a representative interface of a mobile computing device ("master") with an application specific diagnostic device ("slave") via a machine interface.
Figure 6:
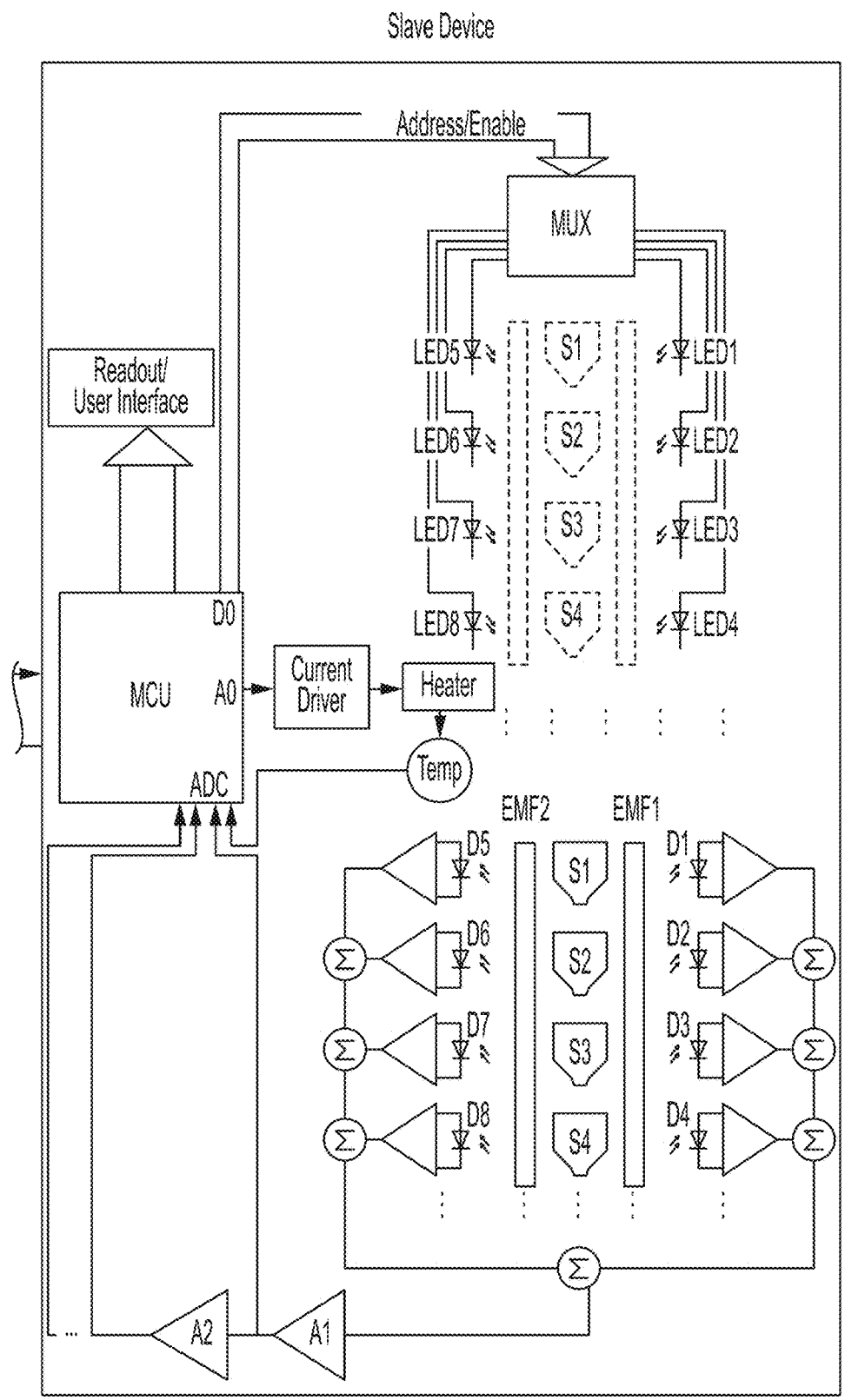

In some embodiments, a single detector, or for example, as shown in FIG. 5, a bank of detectors (D1-D8; which is a non-limiting example illustrating detection of two different optical channels from any of four samples, but the device is not limited to a specific number of detectors or optical channels) measuring all of the emission light from each sample (S1-S4; which is a non-limiting example illustrating four samples, but the device is not limited to a specific number of samples) and optical channel through emission filters (e.g. EMF1 & EMF2) is interfaced through a common summing junction to a single signal processing path, significantly reducing the spatial complexity compared to implementing individual signal processing architecture for each detector, and multiplexing each corresponding signal. Multiplexing is achieved by selective/sequential illumination (time domain multiplexing) of each excitation source (e.g., LED1-LED8) addressing unique samples/optical channels through excitation filters (e.g., EXF1 & EXF2). In some embodiments, see for example FIG. 5, the common signal processing path contains multiple stages of amplification (e.g., A1 and A2) to allow programmable sensitivity using a single microcontroller chip (MCU) that has multiple analog to digital conversion channels internally without the need for additional multiplexing hardware. To improve the signal to noise ratio with a limited incremental cost and complexity, individual detectors can be multiplexed with an analog switch to a common signal processing and readout circuit, using the same addressing signals used for selecting the corresponding light sources. Using this approach, noise from non-specific detectors is not superimposed on the signal, potentially improving the signal to noise ratio. In some embodiments, the device comprises a plurality of detectors. In some embodiments, the device comprises a plurality optical channels. In some embodiments, the device comprises a plurality of emission filters as, for example, described herein.

To enable temperature control for temperature sensitive reactions, a simple feedback control system can be used with a resistive heater and temperature sensor mounted on the aluminum sample receptacle. Readout and user interface can occur by digital communication from microcontroller MCU to display devices, for example by connection to a serial LCD or touch screen display, or through wireless bluetooth connection to an external device such as smart-phone or PC running a custom application which can facilitate incorporation of user controls. The devices can also communicate utilizing the methods described herein.

While FIG. 5 shows a dashed line replicate of sample array S1-S4 being illuminated by the light sources to illustrate the concept in a two dimensional representation, implementation of this multichannel arrangement in a representative three-dimensional embodiment as shown in FIGS. 3 and 4. Non-limiting exemplary embodiments of the devices and the reaction blocks can be seen in FIGS. 1-4 as described herein. Note that in FIG. 3, a rigid mounting block for all of the discrete components is not shown in order to have a clear view of the relative orientation of the various optical components. Thus, in some embodiments, the components are mounted on a rigid block. FIG. 4 illustrates another non-limiting example of a reaction block. Overall this figure is conceptually the same as FIG. 3, except that different LED's are used, there are no excitation filters, and there are some minor changes in device geometry. A device can be configured as described herein.

The present disclosure also provides methods of operating an analytical device designed to detect sequence specific strands of nucleic acid polymers to, for example, enable detection of specific pathogens of interest, or genes indicative of certain physiological or disease states. Such analytical devices are disclosed herein (see, representative embodiments in FIGS. 1-4). The methods described herein, however, can be utilized with any device that utilizes real-time fluorescence-based amplification methods. In some embodiments, the methods are implemented using a mobile computing platform (e.g., Android OS or iOS). In some embodiments, the methods are performed by a computer processor. In some embodiments, the methods are performed by a computer. The computer can be configured or programmed to be run the methods described herein.

In some embodiments, a mobile computing device ("Master"; e.g., smart-phone or tablet with graphical touchscreen user interface) is configured to issue commands wirelessly to a simple microcontroller on an application specific diagnostic device ("Slave"; such as those disclosed herein; see, for example, FIGS. 1-4), which sends back data which is then displayed and managed by the software on the mobile computing device (see, FIG. 5). The slave diagnostic device comprises a host microprocessor (MCU), suitably in its circuit board, which can be, or is, configured to interpret commands from the master mobile computing device (i.e., control the temperature accordingly on an on-board heating block on which diagnostic reactions are controlled, read fluorescence within the sample reactions contained in the device, etc.) or communicate these results back to the mobile computing device, or any combination thereof. The touchscreen on the mobile computing device can also be exploited or configured to enable a rich, user friendly graphical interface, and additional rich features such as GPS and wi-fi is accessed to enhance the practicality of the system. In addition, communications between the master mobile computing device and the slave application specific device can be coded such that multiple slaves can be multiplexed to the same master, algorithms can be used to automatically recognize and deal with losses of communication between devices, and software can be included to help prevent catastrophic thermal failure in the slave device(s).

Hardware integral to the mobile computing platform can readily be leveraged to provide additional value to the user. For example, most smart-phones and tablets come equipped with GPS capability which can be used to easily and automatically record field locations where tests are run, for example as described herein, and access to wi-fi or data networks can be used to automatically send alarms in the case of certain events (e.g., detection of a select biological agent in a sample can automatically be communicated to a quarantine inspection station), or to facilitate sharing of results by e-mail or through remote cloud based servers. Coordination of information across multiple users across vast geospatial scales can be used to automatically generate useful tools such as disease risk maps, especially when coupled with other information systems such as weather conditions and other phenomena influencing disease transmission, progression, and virulence.

As illustrated in FIG. 5, the interface between the master mobile computing device and the slave application specific device can be made using any standard communications hardware and protocol such as, for example, RS232, USB, or bluetooth. These are non-limiting examples and any communication protocol or hardware can be used. In some embodiments, the mobile computing device communicates wirelessly with the application specific device, and interprets and manages all data from the device.

Where communication between devices might be intermittent, especially as might be the case for wireless communication such as bluetooth where the user takes the master device out of range of the slave device, the devices are configured so that both devices can continue operation even in the event of an interruption in communication. Thus, in some embodiments, all instructions originate from commands entered through the user interface on the master device, and the slave device accordingly performs the requested functions (i.e., temperature control, fluorescence and temperature reading, etc.) and returns data for the master device to display and manage. These embodiments would prevent a situation where the master device may crash or "freeze" waiting for expected data to return and, likewise, the slave device might get locked into a routine resulting in catastrophic device failure. As an example of the latter, if updated commands are not issued to the slave device to check the temperature and regulate the power to the heater accordingly, it is conceivably that the slave device can become stuck applying 100% available power to the heater and result in burning out of the heating element, thermal fuses, or otherwise result in significant thermal damage to the device. Thus, the methods described herein can prevent the effects of loss of communication, which could include the loss of critical data.

In some embodiments, to prevent software crashes on the master device due to loss of communication and enable multiplexed interfacing to multiple slave devices, data returned from slave devices is coded with a code for the type of data returned, the particular device sending the data, and the time at which the data was recorded. In some embodiments, the master device no longer has to launch a separate thread for each bit of data that it expects to be returned, but can have a single communication service waiting for any set of coded data to be returned and processing the data accordingly.

Automatic recognition of events where communications are lost is also important for ensuring minimal loss of data and preventing catastrophic failures such as those described above. To this end, the device is configured with a method for the slave device to recognize loss of communication by simply recording the time since the last instruction was received and comparing that to the maximum time expected between instructions. For example, in the real time amplification routine, instructions might be expected on the order of every second to check the temperature and regulate the heater accordingly. If no instructions are received within a reasonable window, the slave device can recognize this as a loss of communication and begin to take more autonomy over its own functions, for example, by recording the observed data locally until a connection is remade and data can be requested again by the master device, and updating its own temperature control algorithm automatically. In some embodiments, either or both the master device and slave device can automatically send a "query" code to the other device and, if an appropriate answer is not returned within an expected window of time, it can be interpreted as a loss of communication. In this event, the user interface on the master device can alert the user that connection was lost, and periodic attempts can be made to recover the connection and send follow up queries. Once the connection is recovered, a request for data stored locally on the slave device can then be sent again, and all of the data recorded while communication was not available can be sent with the appropriate coding to be processed by the master device.

In some embodiments, as an additional protection against catastrophic thermal failure from excessive power to the heater on the slave device, methods on the slave and master can be implemented which automatically recognize unexpected behavior. For example, if the temperature sensor on the slave device becomes disabled or disconnected for any reason, not only will the slave be unable to control the temperature accurately, but it may cause the heater to burn itself out. Temperature control is typically achieved by comparing the desired temperature to the observed temperature, and regulating the power to the heater to keep them equal (i.e. applying more power when the observed temperature is lower than the desired temperature). If the observed temperature is not responsive due to a defect in the temperature measurement, the controller may continue to apply excessive power until thermal failure occurs. While extreme failure and fire might be prevented by hardware such as a thermal fuse connected to the heater block, the devices can be configured with methods that can be automatically designed to recognize failure of the temperature measurement circuit and automatically shut off heater power to prevent additional hardware damage until the problem can be corrected. To identify potential problems in the temperature measurement or heating circuit, the software can compare the recorded temperatures over time to an expected system response based on known system dynamics. For example, initially it is expected that if the temperature is below the desired value, power applied to the heater will result in an increase in temperature over time. If the rate of temperature increase over time doesn't exceed a minimum threshold rate expected under these conditions based empirically on the thermal performance of the system, the software can recognize this as a hardware problem with the heater and/or temperature sensor and automatically shut off power to the heater. Likewise, if the temperature does not settle to within an acceptable limit of the desired setpoint within an acceptable period of time, the device can recognize this as deviant performance and shut off power to the heater until the problem can be identified and corrected.

The methods disclosed herein enable the user to save and select different reaction settings for a specific diagnostic reaction. In some embodiments, the user initiates a selected diagnostic reaction. The reaction can for example, be selected by pushing a button. The button can be a physical button or one that is present on a touch screen. The button does not need to be like that on a keyboard, but can be represented on a screen as an option that can be selected by a user. In some embodiments, when the button is selected or pushed, a command is given to the hardware to select a reaction and to run the reaction according to a set of parameters. The selection of the reaction can also enable functionality during the reaction such that the fluorescence data is recorded, interpreted, and displayed on the screen (e.g., touch screen) in real time. In some embodiments, data from a reaction or a plurality of reactions are automatically recorded, and can be recalled for display by navigating through a menu of available test records stored either locally, on a networked computer system, or on the internet, which can also be referred to as the "cloud."

The devices can be configured to record GPS coordinates for the location of the test, allow the user to enter labels for each sample (e.g., to describe their origins), or send automated alerts by e-mail or text message when certain events occur (i.e., a regulatory sample is determined to be positive for a specific pathogen).

Figure 7:
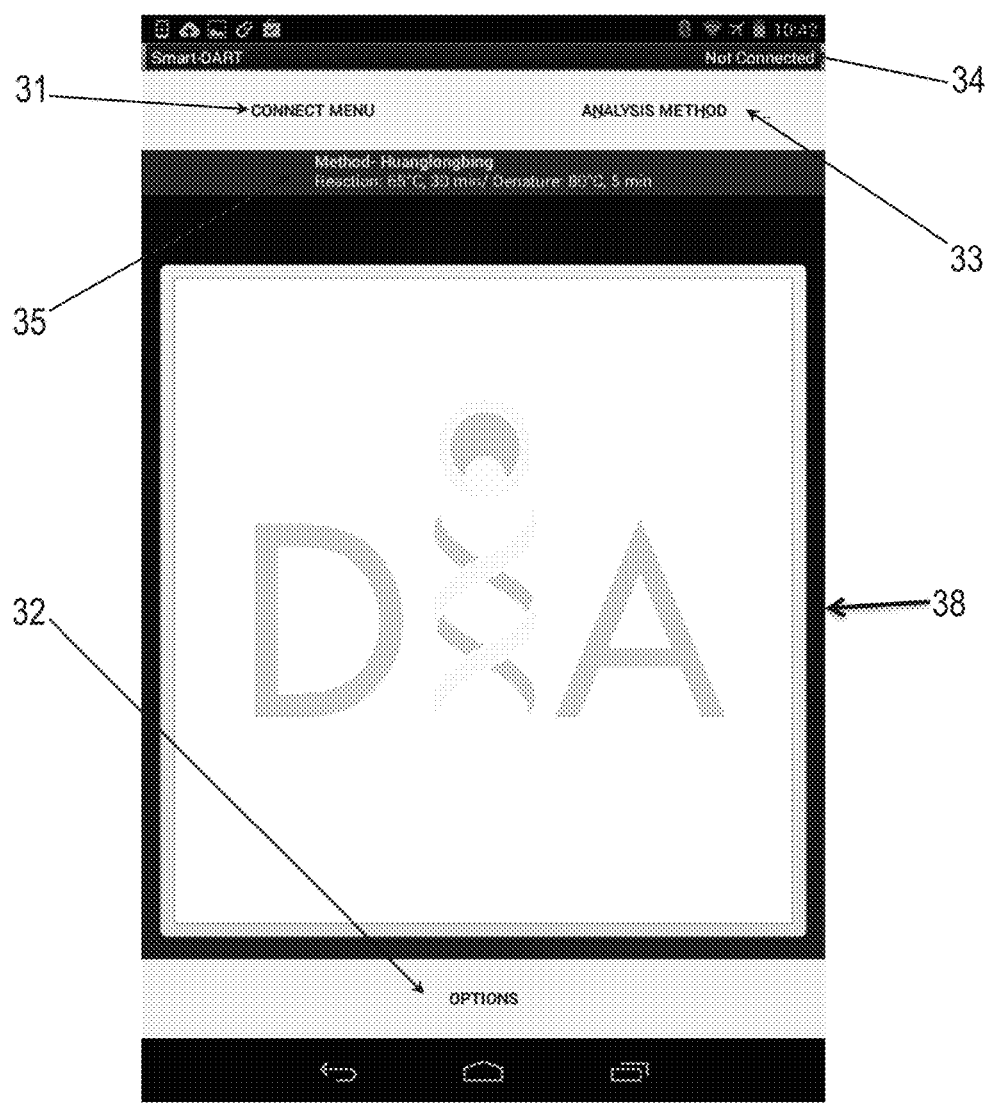
FIG. 7 depicts a representative main/start screen for the mobile application on a mobile computing device to operate the diagnostic device.

Non-limiting examples of implementation of the methods for controlling a diagnostic device based on nucleic acid amplification follow. Representative methods can be implemented as follows. In some embodiments, the machine interface between the mobile computing device and diagnostic device is through wireless bluetooth communication which is ubiquitous on most mobile computing platforms including iOS and Android devices. However, the interface can be through any communication protocol including but not limited to WiFi, cellular, ZigBee®, X10, USB, RS232 and the like. Traditionally, wired interfaces such as USB and RS232 can be bridged through wireless interfaces such as through an addressable radio modem link. The main/start display screen (38) of the application on the mobile computing device would have certain basic options such as those shown in FIG. 7. For example, buttons or touch-pad keys can be displayed on the mobile computing device or touch-screen thereof. Referring to FIG. 7, buttons or touch-pad keys include: "connect menu" (31), which allows the user to proceed to another screen format allowing the choice of particular devices to connect; "options" (32), which allows the user to proceed to another screen format for various parameters (e.g., defining parameters for a specific diagnostic reaction, sharing or displaying recorded results, etc.); and "analysis method" (33), which allows the user to choose the method of analysis and adjust the parameters of analysis for the reactions being performed. In some embodiments, various displays can be present including, but not limited to, "connection" or "power status" (34), which informs the user as the status of the connection or remaining battery charge of the device. In some embodiments, a display "reaction parameters" (35) informs the user of the reaction parameters for the currently selected method.

Figure 8:
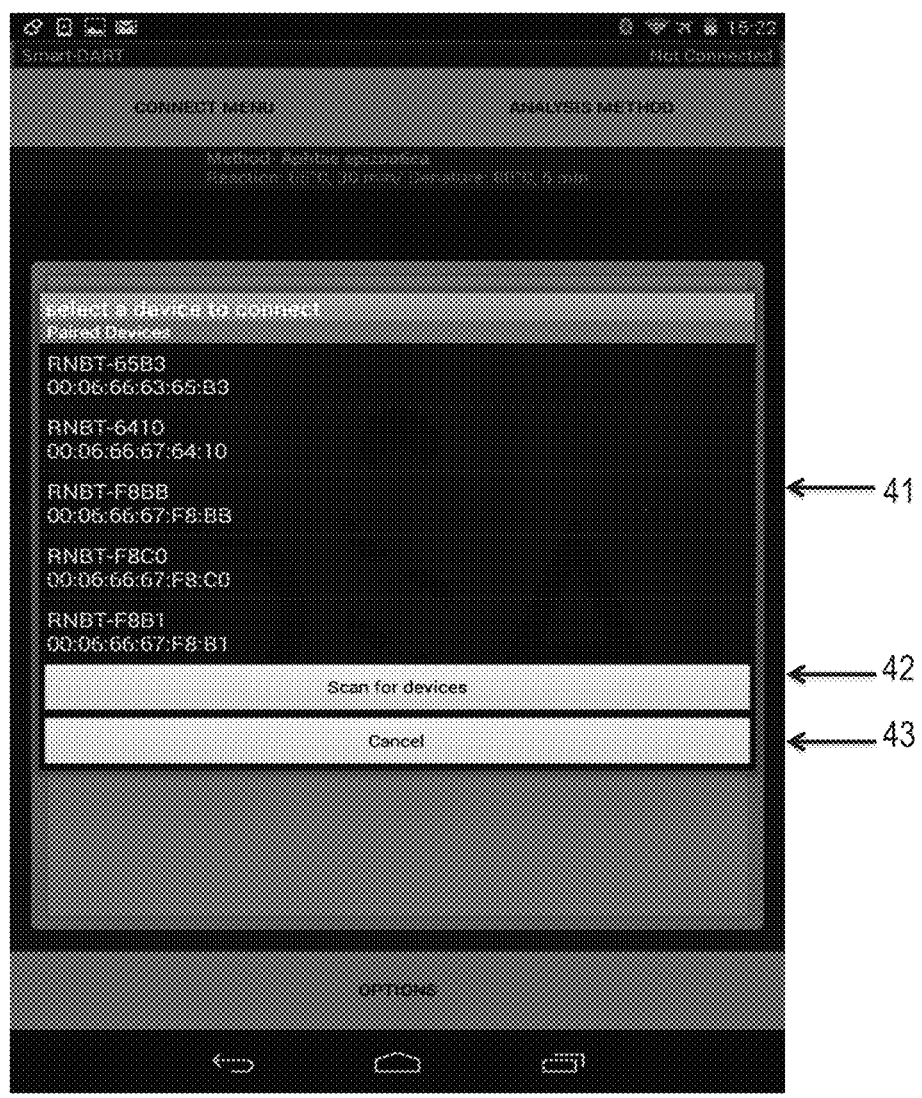
FIG. 8 depicts a representative display screen listing available diagnostic devices to which to connect wirelessly that displays when a user selects "Connect Menu" button; selecting an available device initiates a wireless connection with that device.

Connection to a particular diagnostic device can be made by selecting an available device through the "connect menu" button or touch-key on the mobile computing device. Once the "connect menu" button or touch-key on the mobile computing device is activated, a new display screen (41) showing options for connectable diagnostic devices appears (see, for example, FIG. 8). The desired diagnostic device can be selected accordingly by selecting the appropriate portion of the list. In some embodiments, this screen format also displays a touch-key for scanning for available devices (42), and/or a "cancel" touch-key (43) which re-loads the previous display screen.

Figure 9:
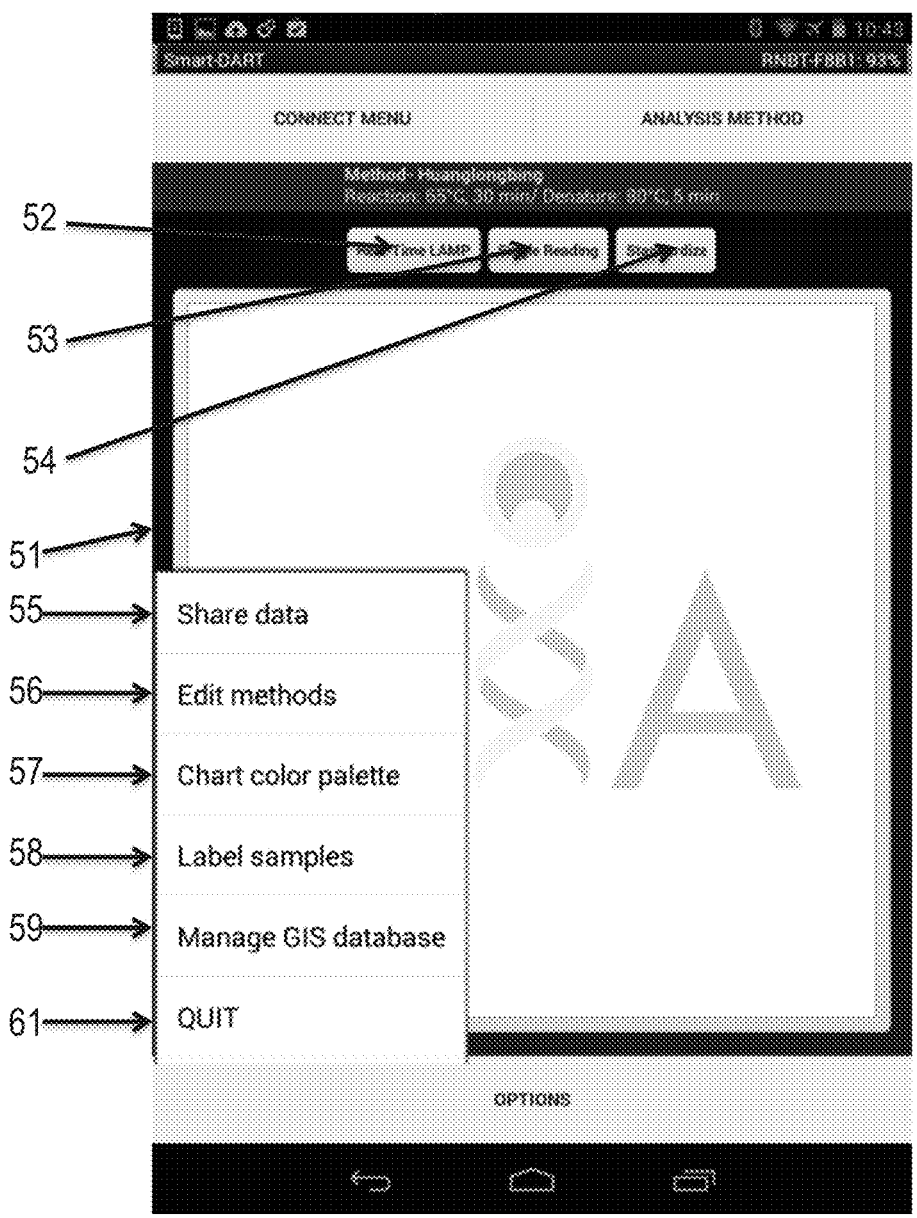
FIG. 9 depicts a representative display screen produced after selecting a desired diagnostic device, as well as additional display screen when selecting the "Edit Methods" touch-key, and a display screen produced after selecting the "Add New Method" touch-key.

Once a desired diagnostic device has been selected and a connection is made to the desired diagnostic device, another display screen (51) is made available to the user. This display screen contains touch-keys for "Real Time LAMP" (52), "Single Reading" (53), and "Standardize" (54) (See, FIG. 9). In some embodiments, when a connection is made to a device, specific details of the connection can be shown on the user interface. These details can include, but are not limited to, the identity (e.g., hardware address or name) of the connected device, and information such as the remaining battery charge on the device. Referring to FIG. 9, by activating a single button on the main screen or by activating the "options" button, a set of additional functions in a drop-down menu appears. The additional functions include, but are not limited to, "Share data" (55), "Edit methods" (56), "Chart-color palette" (57), "Label samples" (58), "Manage GIS database" (59) and "Quit" (61).

Upon selection of the "Edit Methods" option, a new display screen (63) is made available (see FIG. 9). This new display screen lists existing analytical procedures (64). These existing analytical procedures can be deleted or edited, or new analytical procedures can be created. For example, if a user desired to edit a particular analytical procedure, the user would select the desired analytical procedure from the list. A new display screen (not shown) would appear listing parameters that can be edited. If a new analytical procedure is desired to be entered, the user would select the touch-key "Add New Method" (65), upon which a new display screen (67) would be made available. This display screen contains options for various parameters for the new analytical procedure to be added to the list as well as a touch-key keyboard for implementing the same. Such options include touch-keys, and corresponding text boxes, for parameters including, but not limited to, "Lamp Temperature (° C.)" (72), "Lamp Reaction Time (min)" (73), "Denature Temperature (° C.)" (74), "Denature Time (min)" (75), and "Fluorescence Reading Interval (sec)" (76). Touch-keys may also be included for other parameters including, but not limited to, additional temperatures, durations, photodetection gains, and other settings. Selection of a desired touch-key results in the placement of a cursor in the corresponding text box, into which the user enters the desired value using the keyboard. In addition, a "Method Name" (71) text box exists into which the user can enter the name of the new diagnostic procedure by using the keyboard. Once all new diagnostic procedures are entered into the application and/or desired existing diagnostic procedures have been changed, the user may select the touch-key "Quit" (66), upon which the previous display screen (51) would be made available.

Figure 10:
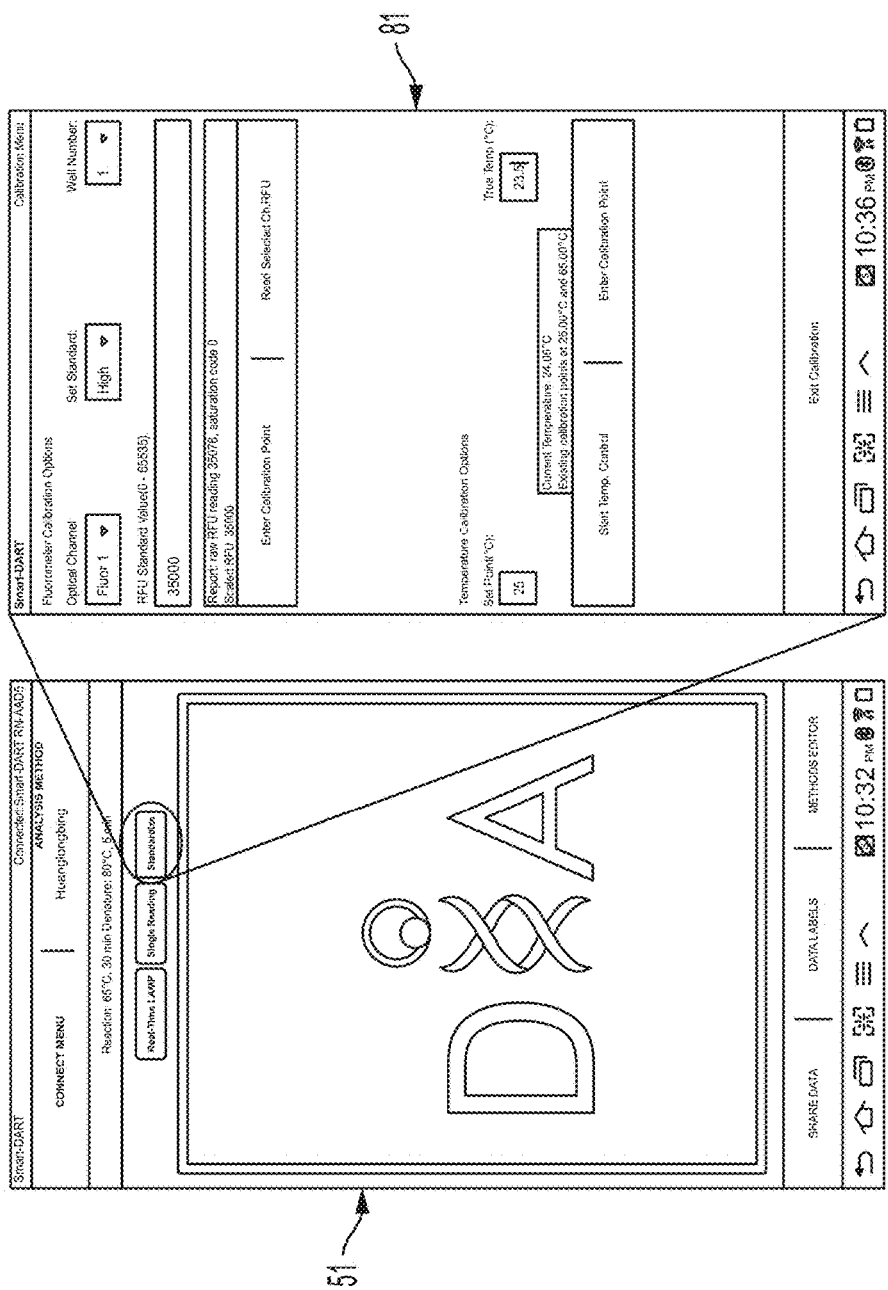
FIG. 10 depicts a representative calibration menu for recalibrating temperature sensor on board the diagnostic device, or to enter arbitrary user designated fluorescence calibration values for fluorescent standard solutions.
Figure 11:
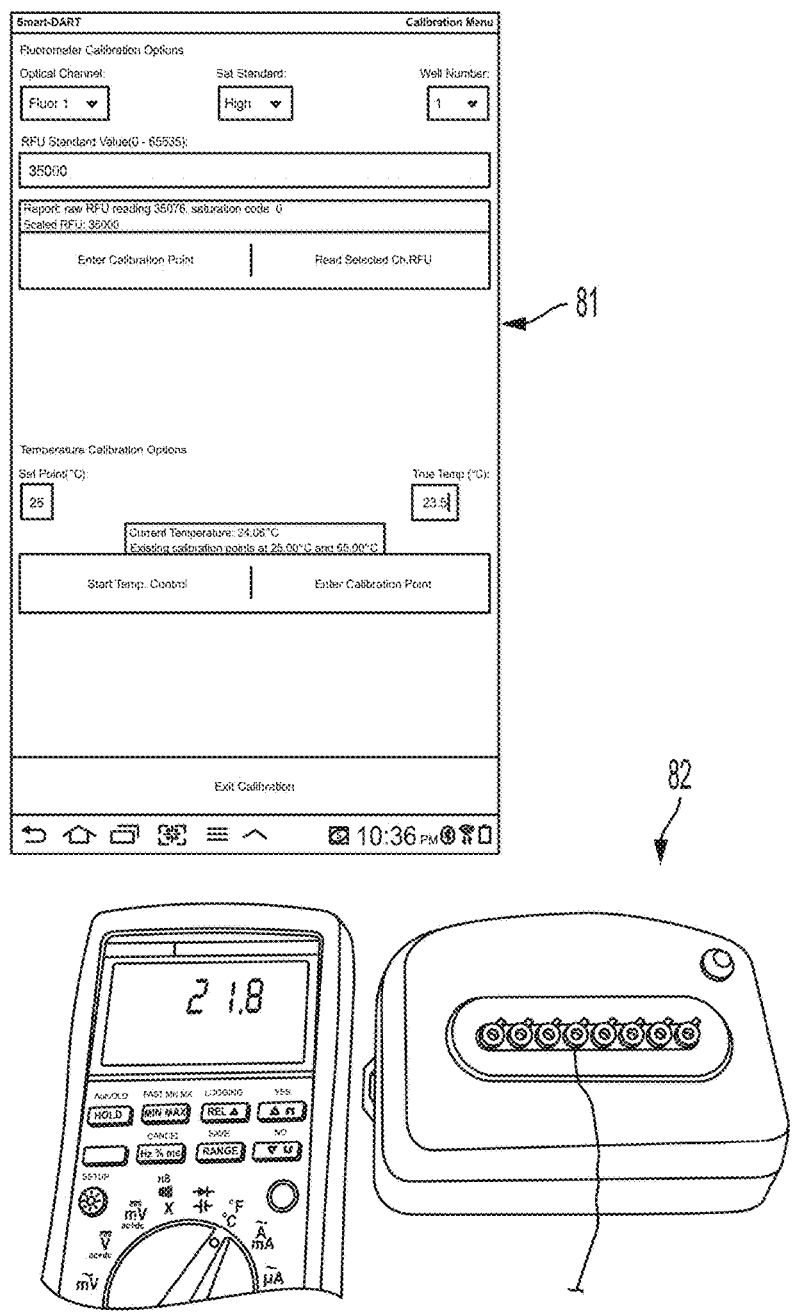
FIG. 11 depicts a representative method for calibrating system temperature sensor to ensure reliable temperature control.

A connected device can be calibrated by a single button navigation, or through an options menu, to a calibration menu, which enables and allows the device temperature sensor to be calibrated to ensure accurate process control. This can also enable the user to define desired reference values for standard samples with a given reference fluorescence intensity. Referring to FIG. 10, for example, a user desiring to calibrate a connected device may select the "Standardize" touch-key from display screen 51, which produces a new display screen (81) which provides a calibration menu. While calibration values can be stored in non-volatile memory (e.g., EEPROM) on the diagnostic device which can be programmed with default values at the factory, recalibration of the temperature can improve accuracy due to variations in temperature measurement hardware and circuitry between devices, and the option for fluorescence calibration enables the user to define desired reference fluorescence values for a given standard. For calibrating temperature, one option is to enable the user to send an instruction for the device to control the temperature to a desired setpoint, and allow the user to program in the actual temperature of the device once steady state temperature is reached and recorded by a reference sensor (82) (see, for example, FIG. 11). The device then can record the actual temperature and the corresponding observed digitized value of the temperature measurement system into EEPROM, and this data can be used to estimate a best fitting calibration equation using a suitable algorithm. This process can be automated to calibrate a device by communicating the values of the external reference temperature sensor directly to the mobile application through any of the methods described above.

Figure 12:
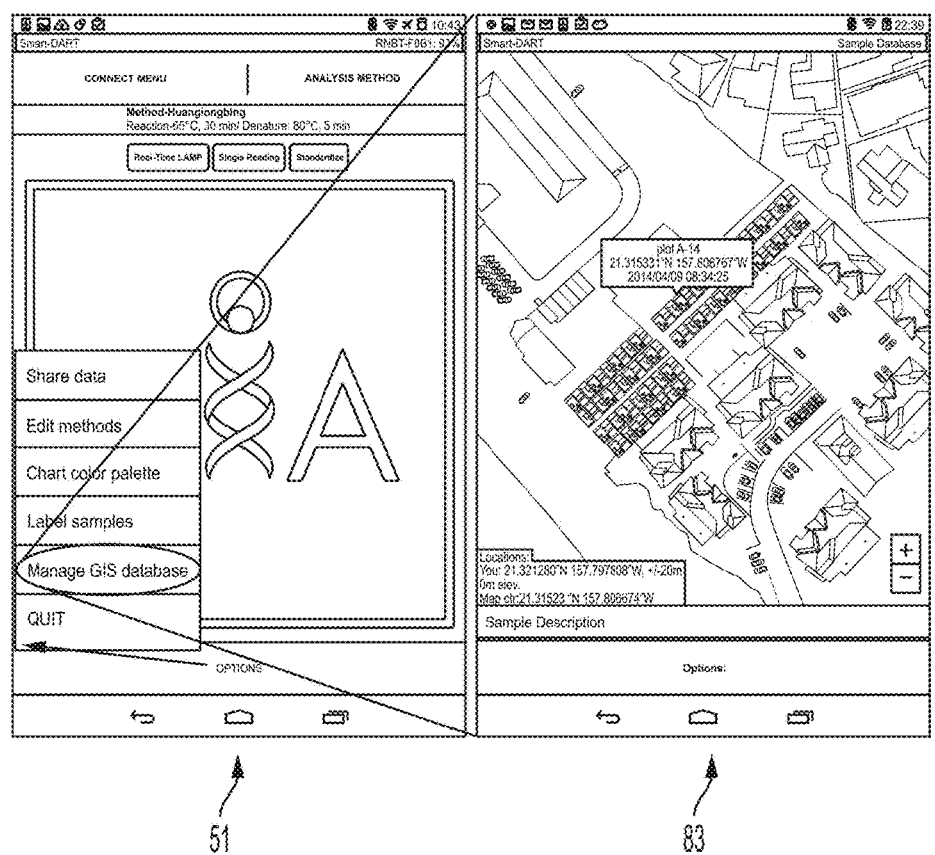
FIG. 12 depicts a representative use of interactive GPS tool to record sample location, time, and description into retrievable database.

To facilitate record keeping and interpretation of results especially with respect to the origin of samples, an interactive map based activity within the mobile application can access GPS sensors to manage a retrievable database of sample locations, times, and descriptions (see, FIG. 12). For example, selecting "Manage GIS database" from the options menu on display screen 51, results in a new display screen (83) which presents a map, parameters such as current time, editable text description, and GPS location can be recorded into the sample database, and entries can be deleted from the database by "long" clicking near the record location on the map. Information in the database can be used to populate drop down menus to simplify the recording of information associated with tested samples.

Figure 13:
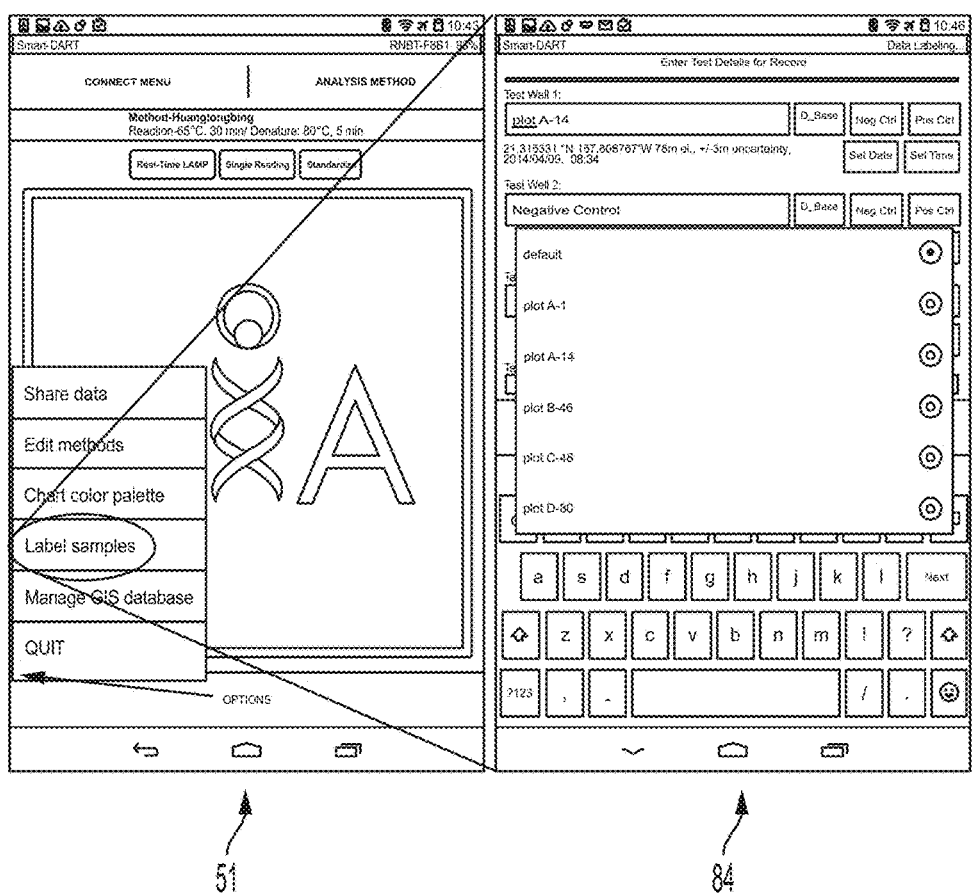
FIG. 13 depicts a representative labeling activity to record information about samples being analyzed, including information stored in GPS database.

In preparation for running a reaction (or in the graphical display window that opens during a reaction; see below), a user can open a new window to enter identifying information for each of the samples being analyzed in the reaction (see, for example, FIG. 13). By selecting the "Label samples" touch-key from the display screen 51, a new display screen (84) is produced, which provides options for data labels. For example, the labels may describe the geographical origin, date and time of collection, or the nature or any other details of the sample being analyzed, and these data are automatically included in the data record of completed tests.

Figure 14:
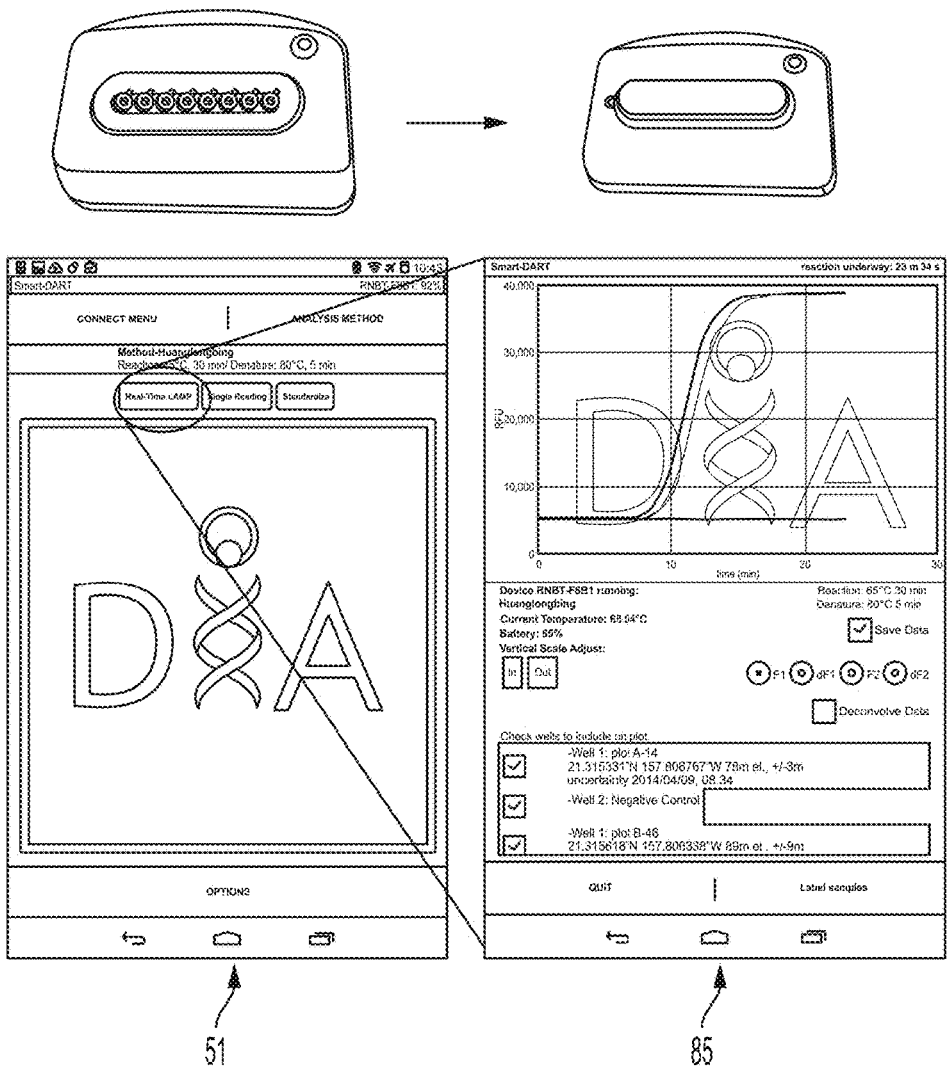
FIG. 14 depicts a representative initiation of a diagnostic reaction, and the ensuing real-time display of results of diagnostic reactions in heldheld instrument.
Figure 15:
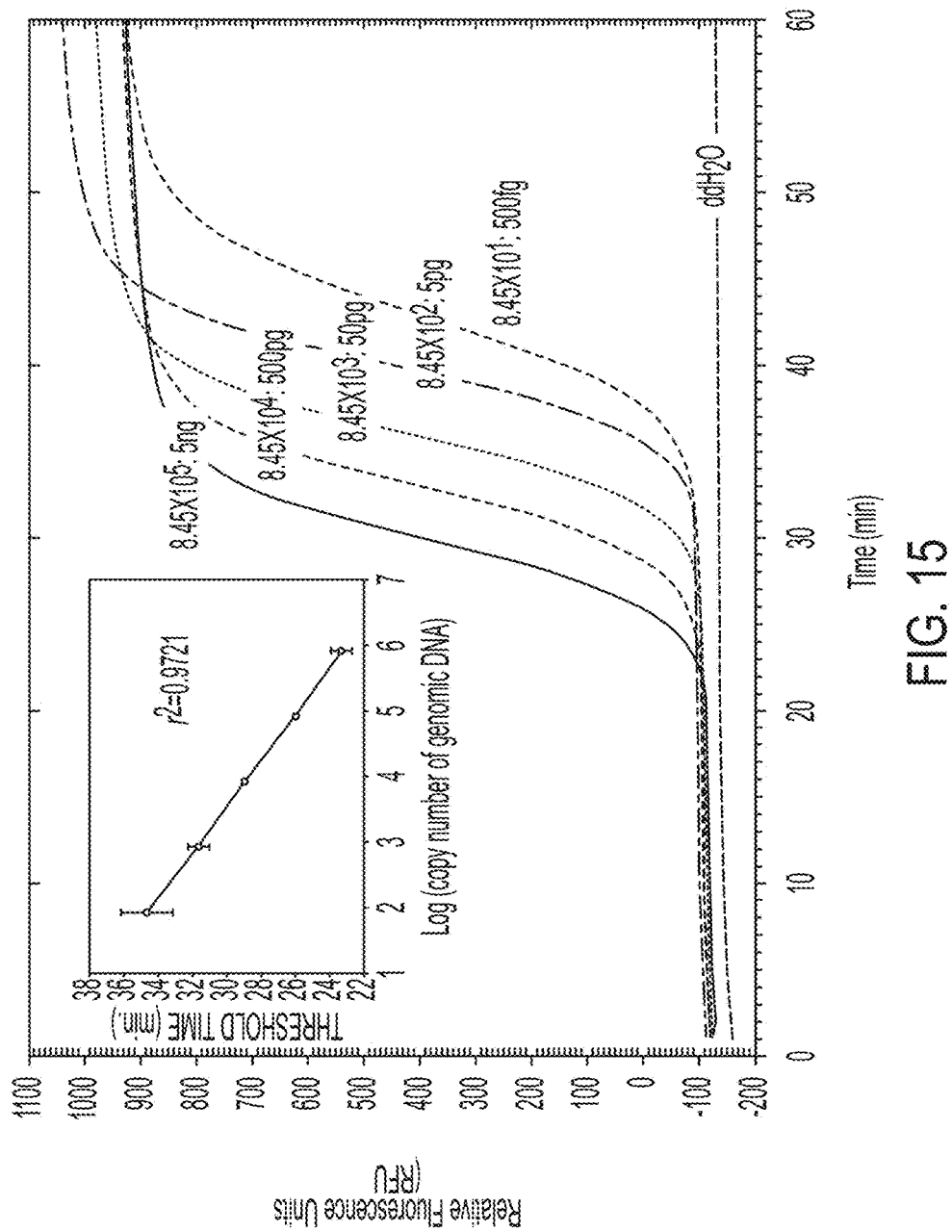
FIG. 15 depicts a representative menu to share available results by e-mail or to/from on-line cloud based directory, display recorded amplification results graphically, or color coded test results on an interactive map.

A suitably calibrated instrument connected to the mobile computing device can be used to run a real-time diagnostic reaction by selecting a single button or touch-key (see, for example, FIG. 14). For example, selection of the "Real Time LAMP" button or touch-key 52 produces a new display screen (85). In this activity, real time fluorescence data can be displayed for each sample, and the graphical data can easily be interpreted by the user to determine whether the sample does or does not contain the sequence of interest, for example, a positive sample that initiates an amplification reaction will result in an easily identifiable sigmoidal increase in fluorescence over time (see, for example, FIG. 15). To facilitate interpretation of each sample, check boxes are available to alternatively display or hide data from each sample in real time, to display results from different optical channels when multiplexed reactions using different fluorescent spectra are used (i.e., to run positive internal control reactions for spiked segments of control DNA, or to identify multiple target sequences simultaneously in the same reaction). On the main screen, any of the available methods can be selected from the corresponding drop down list, and when the user "starts" a reaction the corresponding reaction parameters are used, and the reaction name can be recorded in the results along with other user entered information describing the origin and description of individual samples being tested.

As an alternative to facilitate analysis of results, the rate of fluorescence change over time can be displayed which results in a characteristic spike for samples containing the target DNA. The interactive display can also enable the user to apply different mathematical analyses of data, for example to deconvolve observed fluorescence signals from different optical channels to infer unique contributions of fluorophores with overlapping fluorescence spectra. Automated classification algorithms in the software can identify which samples are positive for individual reactions for easy reference. In one example, a least squares regression curve is fit through the fluorescence data over time, and a sample is scored as positive for presence of the target DNA when fluorescence values are observed to increase by a certain threshold value from the projection over several successive observations, where the threshold value is based on a running estimate of the background noise around the best fit curve. Similarly, the classification algorithm might classify a sample as positive when the rate of change of fluorescence exceeds a unique maximum value that exceeds the average rate of change by a given threshold number of standard deviations.

The "threshold time" at which samples are observed to show unambiguous signs of amplification can also be used to automatically infer quantitative information about the number of copies of the target DNA sequence in the original sample, using approaches analogous to well established protocols of quantitative PCR. Because the amplification reaction is exponential in nature, the time at which a given threshold copy number of amplicons can be observed (proportional to the observed fluorescence) is mathematically related to the initial copy number of the sequence. These quantities can be correlated through the known relationship, and used to develop a calibration equation to estimate the copy number in the sample from the observed threshold time.

Figure 16:
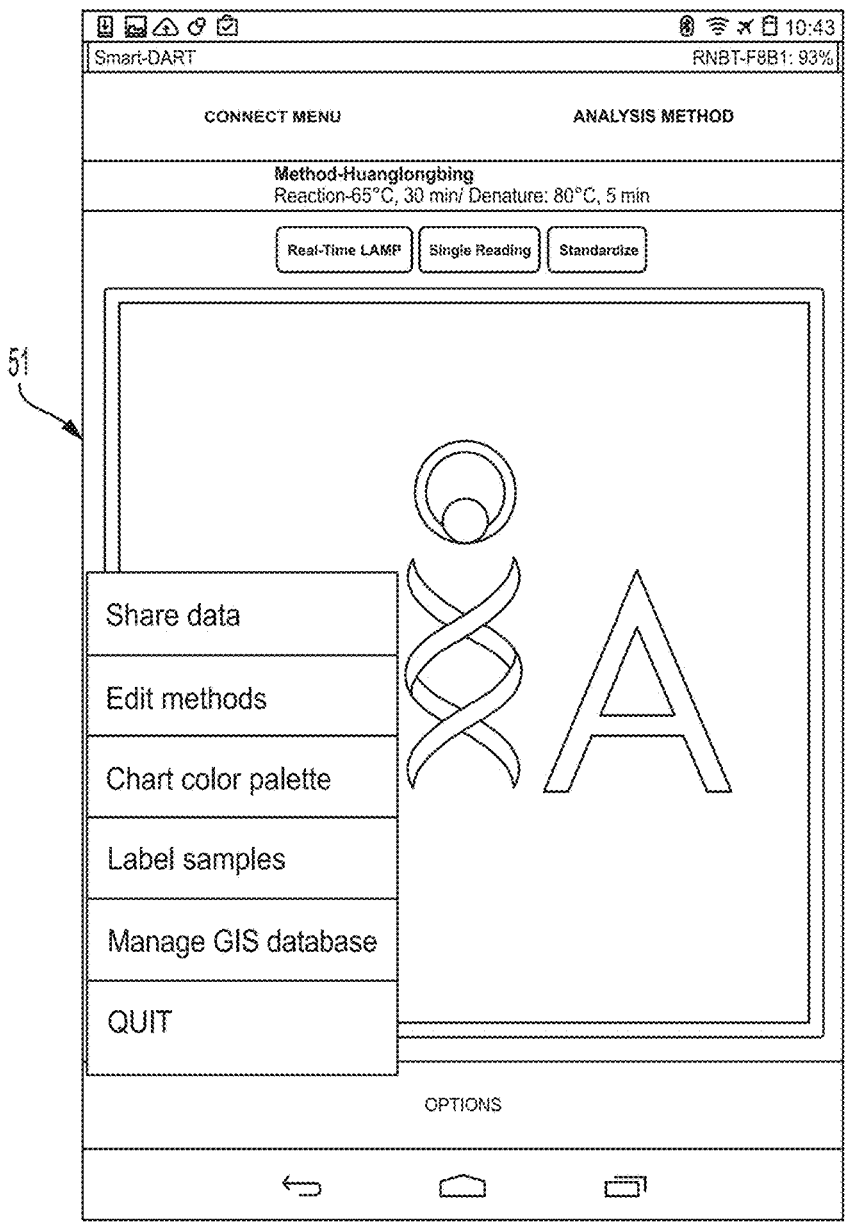
FIG. 16 shows quantitation of gene copy numbers in sample from observed threshold time for amplification.
Figure 16:
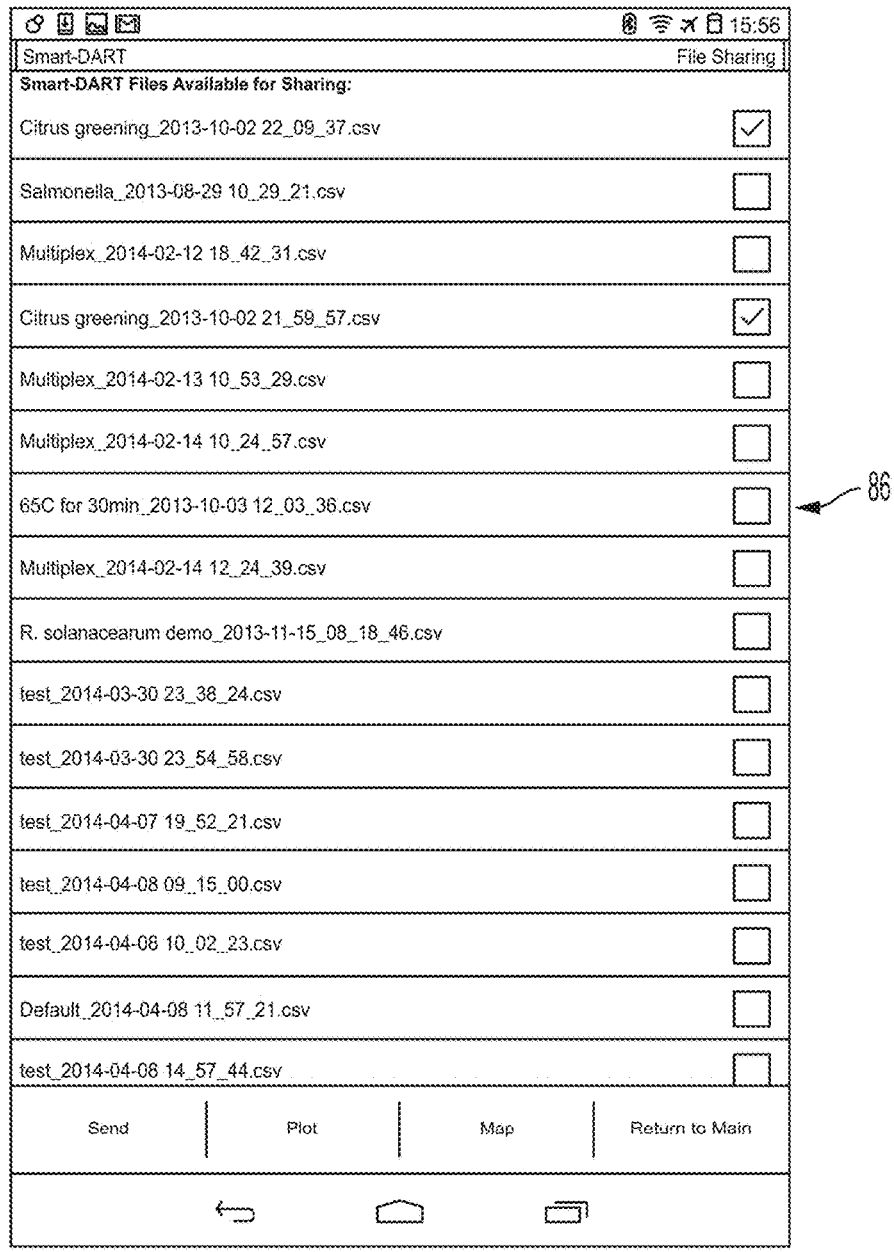
Figure 16:
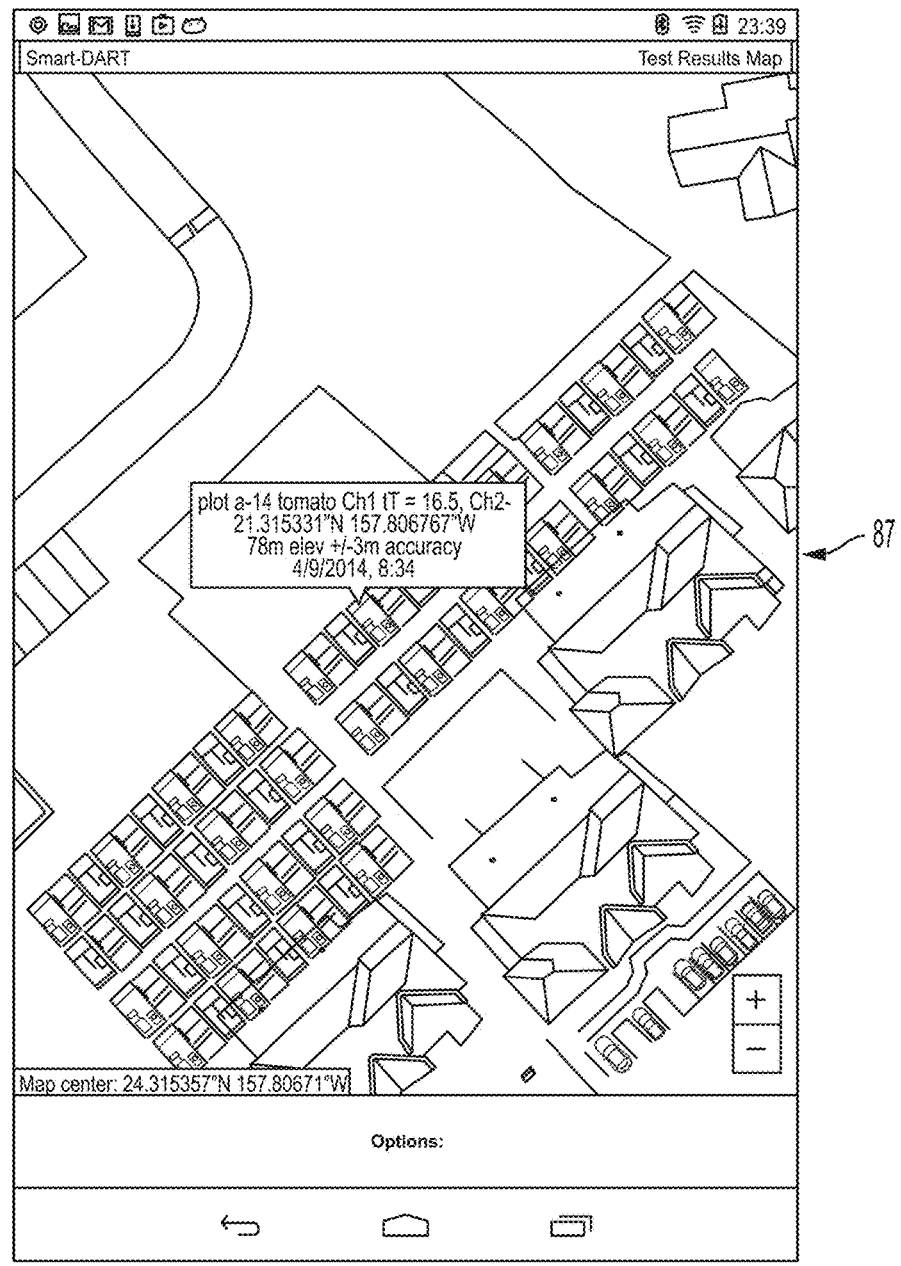

After reaction results are complete and data is stored on the device, the user can select from display screen 51 the "Share data" touch-key to navigate to a new display screen (86) showing a menu of available data files for sharing or display (see, FIG. 16). In the example application, recorded data can be selected to be displayed graphically. Display of test results may include graphical representation of amplification results, text summaries of test results including inference of presence of target nucleic acid sequences, color coded test results on an interactive map, or any combination thereof. Alternately, selected test results can be shared as e-mail attachments or to a directory on a remote server, as depicted in new screen display (87). The device can be configured to perform any or all of these functions.

In some embodiments, the method is used to control the temperature on the heating block of the diagnostic instrument. In some embodiments, the method instructs the machine to do a single read of the fluorescence values observed on each channel of the device. A calibration menu can allow the user to perform a temperature calibration of the temperature sensor, or enter their own arbitrary fluorescence calibration on the diagnostic device.

The device can also be used in methods for taking real-time fluorescence measurements from an array of samples or optical channels during a nucleic acid amplification or other analytical process. The measurements can be multiplexed in the time domain by sequentially illuminating an array of rigidly fixed light sources addressing individual samples or optical channels. The measurements can then be multiplexed according to the descriptions and components contained herein. The luminescence from the samples and/or optical channels in the real-time fluorescence analysis system are detected by a single detector or detector array interfaced to a common (e.g., single) signal processing pathway. The single detector or common pathway can then be analyzed to provide a result to the user.

The device can be constructed to ensure minimal water and dust penetration. Thus, referring to FIG. 1, a gasket can be used at any desired interface between components.

The above embodiments with reference to particular Figures are only representative of the numerous embodiments within the scope of the subject matter presented herein. Each of the options and functions described above can ultimately originate from any number of display screens and need not be presented to the user in the order or hierarchy set forth above and in the accompanying Figures. The flow chart presented in FIG. 17 simply lists the various options encompassed within the application for the mobile computing device. Each of the parameters can be implemented in any desired order and can be implemented by activating a button on the mobile communication device itself, or via a touch-key within a particular display screen of the application.

Figure 17:
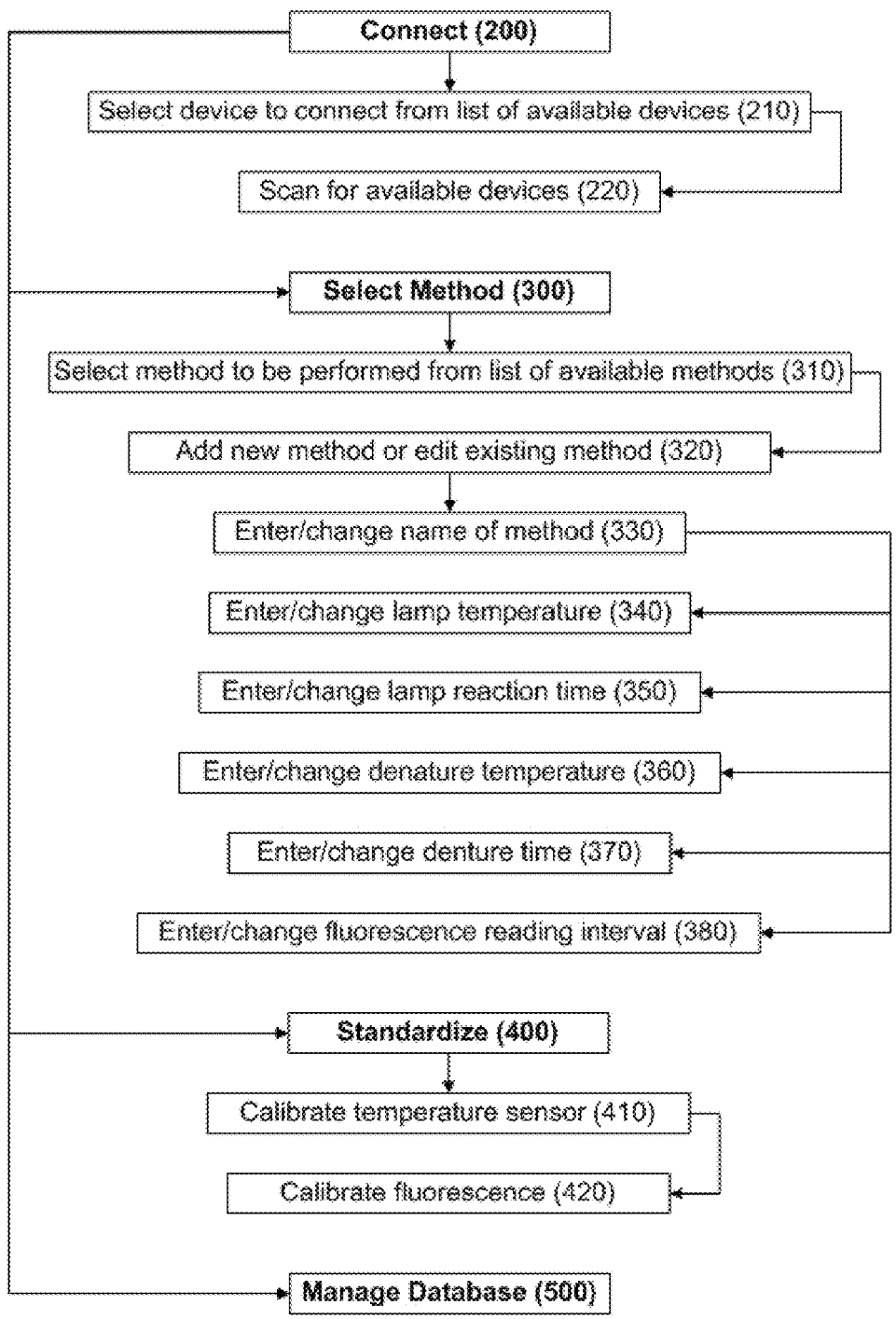
FIG. 17 depicts a flowchart listing various options of the application loaded on to a mobile computing device.

Referring to FIG. 17, several functional steps are shown including "Connect" (200), "Select Method" (300), "Standardize" (400), "Manage Database" (500), "Label Sample" (600), "Real Time Diagnostic" (700), and "Share Data"

(800). Of course, the names of these functional steps, as well as the names of any options on any menu or display screen can be changed to any desired name. Further, these functional steps need not be performed in any particular order and any subset of the functional steps can be performed. Thus, not every step need be performed. For example, the standardization step(s) need not always be performed prior to performing a diagnostic procedure on a sample; likewise for the other optional steps.

Several options exist for the "Connect" step including, but not limited to, selecting a device to connect from a list of available devices (210) and scanning for available devices (220).

Several options exist for the "Select Method" step including, but not limited to, selecting a method to be performed from a list of available methods (310) and adding a new method or editing an existing method (220). When desiring to enter a new method or edit an existing method, several options exist including, but not limited to, entering or changing a name of a method (330), entering or changing the lamp temperature (340), entering or changing the lamp reaction time (350), entering or changing the denature temperature (360), entering or changing the denature time (370), and entering or changing the fluorescence reading interval (380).

Several options exist for the "Standardize" step including, but not limited to, calibrating the temperature sensor (410) and calibrating fluorescence (420).

Several options exist for the "Manage Database" step including, but not limited to, listing database entries for samples (510) and entering database information (520). When desiring to enter new database information, additional options exist including, but not limited to, GPS location (530) and editable text description (540).

Several options exist for the "Label Sample" step including, but not limited to, entering identifying information for a new sample (610). When desiring to enter new sample information, additional options exist including, but not limited to, geographic origin (620), date and time of collection (630), and details regarding the sample (640).

Several options exist for the "Real Time Diagnostic" step including, but not limited to, performing a diagnostic method on the sample (710), displaying real-time fluorescence data for the sample (720), and providing mathematical analysis options (730).

Several options exist for the "Share Data" step including, but not limited to, providing a list of data files (810) and sharing the data files via email (820).

In order that the subject matter disclosed herein may be more efficiently understood, examples are provided below. It should be understood that these examples are for illustrative purposes only and are not to be construed as limiting the claimed subject matter in any manner

EXAMPLES

Example 1

Detection of *Candidatus liberbacter* in Psyllids using Smart-DART Platform

Application with Portable Computing Device and Diagnostic Device.
Sample Preparation:

Fresh psyllids are collected into vials containing 95.0% ethanol using an aspirator. A clean bench top with clean disposable paper service is used. Disposable gloves are worn. Eight filter paper pieces are prepared and 1-20 psyllids are laced onto each filter paper piece. The psyllids are air dried for 5 minutes. A white 8-tube PCR strip is placed on a rack. Fifty (50.0) µl of extraction buffer (20 mM Tris-HCl, pH 8.0 containing 2 mM EDTA and 1.0% Triton-X100) is pipetted into each tube, and the cap is closed. One tube at a time is opened and all dried psyllids from the corresponding filter paper are dropped into the tube and the cap is closed. Sample information (psyllid number and origin) is recorded for each labeled tube. An 8-tube PCR strip is placed into a Smart-DART unit and heated to 85-95° C. for 5-10 minutes. This can be achieved, for example, by defining a new method "sample prep" in the Smart-DART application to heat to the desired temperature for the desired duration. The white 8-tube strip is placed back on the rack. Gloves are changed and the clear 8-tube PCR strip is placed next to it. Fifteen (15.0) µl of amplification master mix is placed into each tube using a new pippette tip for each tube. Five (5.0) µl of primer and probe mix are placed into each tube using a new pipette tip for each tube. Opening one tube at a time, five (5.0) µl of sample is transferred from each white tube to the corresponding clear tube. The pipette tip is discarded and a new pipette tip is used for the next sample (psyllid extraction). The clear 8-tube strip is placed into a Smart-DART™ for analysis.

Runing the Test to Test for *Candidatus liberbacter* using Smart-DART™ Platform (1) Opening the Smart-DART™ Application and Connecting to Smart-DART Device First, the Smart-DART™ Application is opened on the Android device. One skilled in the art can navigate to the list of applications on most Android devices by clicking on the application menu icon on the home screen, which often looks like a two dimensional array of boxes stacked on each other. Applications are listed alphabetically; the Smart-DART Application can be found and selected by clicking on it.

The "connect button" on the interface can be clicked, and a dialog will pop-up showing connection options. The menu will show a list of paired devices (note that the Smart-DART device uses the Roving Networks RN-42 bluetooth modem, so default device names use the RN neumonic with a 4 digit hardware ID). Any of these can be clicked to connect to the respective device (note pairing does not imply that a device is powered and within range of connection- if it is not the connection will fail). To connect to an unpaired device, the "scan for devices" button can be selected and Android will populate an "unpaired" devices list with available Bluetooth devices in the area. When an unpaired device is selected, the Application will request a pairing key (the default for Smart-DART is "1234"), and then connect if the correct key is provided. If connection is successful, additional controls will become visible immediately below the connect button to calibrate and execute analyses with the specific Smart-DART device.

(2) Creating and Editing Methods

Initially, Smart-DART is programmed with a default method for running a generic LAMP reaction (30 minute reaction at 65° C. with fluorescence read every 30 seconds followed by a 5 minute denature step at 80° C.). The methods database can be added to and/or edited by clicking the "methods editor" under "Options" at the bottom of the screen. Within the methods editor, a method in the list may be edited by clicking on it, or deleted by "long" clicking on it. Alternately, a new method can be defined by clicking the button at the lower right side of the methods editor.

The method to use for an analysis can be changed by clicking the "method select" button at the top right of the main screen. A pop-up list containing all of the currently defined methods in the database will then be available from which to select. The reaction parameters for the currently selected method will be displayed in the underlying text field.

(3) Entering Data Labels for Samples

When real-time analysis of a set of samples is complete, labels corresponding to each sample are recorded to the saved data file. The information within these labels can be changed before or during a reaction by clicking the "data labels" button on the corresponding window. Within the labeling activity, the positive or negative buttons to the right of each text field can be selected to populate the field with "positive control" or "negative control", or desirable text may be entered within the field to describe the sample. The "D_base" button for each sample may be selected to open a drop down list of locations, times, and sample descriptions available in the application's GIS database, which can be populated in an interactive map based activity accessing GPS positions (to manage or add to the GIS database, "Manage GIS Database" under "Options" on the home screen may be selected). "Accept labels" may be selected upon completion, upon which the preceding window will be returned.

(4) Running Real-Time Reactions on Smart-DART

When a suitable method is selected and a Smart-DART hardware device is connected, load samples into the Smart-DART device (wells are numbered from 1 to 8 in order from the side of the device nearer to the power jack and farthest from the LED), put the lid on, and click the "Real-Time LAMP" button under the "connect menu". Analysis will automatically be started, with data displayed graphically in real-time as the reaction progresses. The real-time window also displays the current device temperature, the time the reaction has been going, the name of the method, and corresponding reaction parameters/times being used. There are also controls to select which data are visible, and to save the results of the current analysis to file. If the reaction is not already completed, the reaction is stopped and data is written to the file when the "quit" button is clicked (after a suitable query to make sure that the user really wants to quit).

(5) Sharing Data Through Data Connection

Data for each recorded reaction is stored as a comma delimited spreadsheet file in a Diagenetix directory on the Android device, and these files can easily be shared with others directly through the app. Simply click the "share data" button, click on the files you wish to share (which currently are named and organized chronologically by date and time), and click "send" and you will be navigated to your chosen e-mail program with the files attached. Alternatively in the sharing activity you can view the amplification curves graphically by selecting "plot" for a given checked data file, or if samples within data files have GPS information encoded for them color coded test results can be displayed on an interactive map by clicking "map" after checking the desired files.

Example 2

Detection of *Ralstonia solanacearum* in Wilted Plant Tissue using Smart-DART Platform (Application with Portable Computing Device and Diagnostic Device)

A piece of wilted plant tissue is collected and placed into one tube from the strip of 8 PCR tubes (e.g. white PCR tubes). A half inch section of freshly budded tissue is preferable, but similarly sized sections of stem or leaf tissue can be used. A clean bench top with clean disposable paper service are used and disposable gloves are worn. To each sample tube is added 100.0-200.0 μl of extraction buffer (20 mM Tri-HCl, pH 8.0, 2 mM EDTA) and the samples are allowed to sit in the extraction buffer for 10 minutes. The samples are gently mixed, placed into a Smart-DART unit, and heated to 85-95° C. for 5-10 minutes. A dilution series is made if needed using the extraction buffer. A new pair of gloves is used and the clear 8-tube PCR strip is placed on a rack. Into each tube, 15.0 μl of amplification master mix is pipetted using a new pipette tip for each tube. Into each tube, 5.0 μl of primer and probe mix is pipetted using a new pipette tip for each tube. From each tube in the white strip, 5.0 μl of supernatant is tranferred to the corresponding tube of the clear 8-tube strip. The clear 8-tube strip is inserted into a Smart-DART™ for analysis and the test for detection Ralstonia solanacearum in plant tissue using Smart-DART™ Platform is performed. Similar steps can be used for detection of *Candidatus liberbacter* in psyllids.

Example 3

Detection of *Ralstonia solanacearum* in Irrigation Water using Smart-DART Platform (Application with Portable Computing Device and Diagnostic Device)

Sample Preparation:

Irrigation water sample is collected into a 1.5 ml centrifuge tube. A clean bench top with clean disposable paper service is used and disposable gloves are worn. Water samples are transferred to commercially available centrifugal filter unit with 0.4 μm pore size PVDF membrane. The water samples are centrifuged with desk-top centrifuge machine for 5 minutes and wash filtered two times with 500.0 μl of extraction buffer (20 mM Tri-HCl, pH 8.0, 2 mM EDTA). The PVDF filter is removed from the column, placed into white 8-tube PCR strip, and 50.0 μl of extraction buffer is added. The PVDF filter and extraction buffer are mixed vigorously and the white 8-tube PCR strip is placed into a Smart-DART unit and heated to 85-95° C. for 5-10 minutes. A dilution series is made if needed using the extraction buffer. A new pair of gloves is used to place the clear 8-tube PCR strip on a rack. Into each clear tube, 15.0 μl of amplification master mix is pipetted using a new pipette tip for each tube. Into each clear tube, 5.0 μl of primer and probe mix is pipetted using a new pipette tip for each tube. From each extraction tube, 5.0 μl of supernatant of samples is applied in the white 8-tube strip to the corresponding tube of the clear 8-tube strip. The clear 8-tube strip is placed in a Smart-DART™ for analysis, and the test for detection of Ralstonia solanacearum in irrigation water is performed using the Smart-DART™ Platform.

Similar steps can be used for detection of *Candidatus liberbacter* in psyllids.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed:

1. A device configured for detection of amplified nucleic acid molecules comprising:
 a first housing unit and a second housing unit, wherein the first and second housing units are connectable to each other by a fastener, wherein the interface between the first and second housing units comprises a gasket;
 wherein the connected first and second housing units enclose the following:
  a) a reaction block;
  b) a circuit board electronically connected to the reaction block; and
  c) a battery electronically connected to the circuit board;
 wherein the first housing unit comprises an access area for communication with the reaction block, wherein the reaction block comprises:
 a first bank of light source and a second bank of light source on opposite sides of a heated receptacle, wherein the heated receptacle comprises a plurality of transverse orifices, and wherein the heated receptacle comprises a plurality of bottom portals;
 a first and second excitation filter in light communication between the first bank of light source and the plurality of transverse orifices of the heated receptacle and second bank of light source and the plurality of transverse orifices of the heated receptacle, respectively;
 a first detector bank and a second detector bank in light communication with the plurality of bottom portals of the heated receptacle; and
 a first emission filter and a second emission filter in light communication between the plurality of bottom portals of the heated receptacle and the first detector bank and a second detector bank, respectively;
 wherein the first housing unit comprises a reaction lid closing off the access with the reaction block;
 wherein one of the first and second housing units comprises an on/off switch; and
 wherein one of the first and second housing units comprises a power plug.

2. The device of claim 1 wherein the first or second housing unit further comprises an indicator light.

3. The device of claim 2 the indicator light is an LED indicator light connected to the first housing unit, wherein a gasket is between the housing unit and the LED indicator light.

4. The device of claim 1, wherein the reaction block further comprises reaction tubes.

5. The device of claim 1, wherein the power plug and on/off switch are each connected to the second housing unit, each having a gasket at their interface with the housing unit.

6. The device of claim 1, wherein:
 the first bank of light source is a first excitation LED panel affixed to a first optic housing unit;
 the second bank of light source is a second excitation LED panel affixed to a second optic housing unit;
 a filter holder containing a first emission filter and the second emission filters and the filter holder connects the bottom portions of the first and second housing units; and
 wherein in the reaction block comprises an upper cover comprising one or more gaskets, wherein the upper cover connects the top portions of both the first and second optic housing units and the heating receptacle comprises one or more reaction tube wells.

7. The device of claim 6 wherein the heating receptacle comprises an embedded temperature sensor and an actuator to regulate temperature.

8. The device of claim 7 wherein the temperature sensor is a thermocouple, and the actuator is a polyimide film heater.

9. The device of claim 1, wherein each of the first and second excitation LED panels are affixed to the first and second optic housing unit, respectively, with a fastener.

10. A method of detecting and analyzing fluorescent signals comprising performing a plurality of amplifications of nucleic acid molecules and detecting and analyzing the signals with a diagnostic device of claim 1, wherein the diagnostic device is operated by an application loaded onto a mobile computing device.

11. The method of claim 10 wherein a user selects an analytical device which to connect to the mobile computing device.

12. The method of claim 10 wherein a user scans for available analytical device which to connect to the mobile computing device.

13. The method of claim 10, wherein a user selects a method to be performed from a list of available methods.

14. The method of claim 10, wherein a user selects and edits an existing method from a list of available methods or adds a new method to be performed to a list of available methods.

15. The method of claim 14 wherein the user inserts new or changed entries for one or more of the following: name of method, lamp temperature, lamp reaction time, denature temperature, denature time, and fluorescence reading interval.

16. The method of claim 10, wherein a user standardizes the diagnostic device.

17. The method of claim 10, wherein the user starts a diagnostic method on the sample.

18. The method of claim 17 further comprising displaying real-time fluorescence data for a sample and/or displaying mathematical analysis options for the user.

* * * * *